(12) United States Patent
Willetts et al.

(10) Patent No.: US 8,569,301 B2
(45) Date of Patent: Oct. 29, 2013

(54) 6,6-DIOXO-6-THIA-1,4-DIAZA-NAPHTHALENES AS HERBICIDES

(75) Inventors: Nigel James Willetts, Bracknell (GB); Nicholas Phillip Mulholland, Bracknell (GB); Paul Anthony Worthington, Bracknell (GB); Alaric James Avery, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 0 days.

(21) Appl. No.: 13/320,419

(22) PCT Filed: May 6, 2010

(86) PCT No.: PCT/GB2010/000892
§ 371 (c)(1),
(2), (4) Date: Jan. 23, 2012

(87) PCT Pub. No.: WO2010/130970
PCT Pub. Date: Nov. 18, 2010

(65) Prior Publication Data
US 2012/0115726 A1    May 10, 2012

(30) Foreign Application Priority Data
May 14, 2009    (GB) .................................. 0908293.4

(51) Int. Cl.
*A61K 31/495* (2006.01)
(52) U.S. Cl.
USPC ............................ 514/249; 544/350; 544/406

(58) Field of Classification Search
USPC .................................. 514/249; 544/350, 406
See application file for complete search history.

(56) References Cited

U.S. PATENT DOCUMENTS 3,845,044 A    10/1974  Tong
4,824,474 A     4/1989  Numata et al.

FOREIGN PATENT DOCUMENTS

WO    2009063180    5/2009

*Primary Examiner* — Douglas M Willis
(74) *Attorney, Agent, or Firm* — James Cueva

(57) ABSTRACT

The present invention relates to 6,6-dioxo-6-thia-1,4-diaza-naphthalene derivatives of formula (I) where $R^1$, $R^2$, $R^{3a}$, $R^{3b}$, $R^4$ and $R^5$ are as defined in claim 1; or a salt or N-oxide thereof. Furthermore, the present invention relates to processes and intermediates for making compounds of formula (I), to herbicidal compositions comprising compounds of formula (I) and to methods of using compounds of formula (I) to control plant growth.

(I)

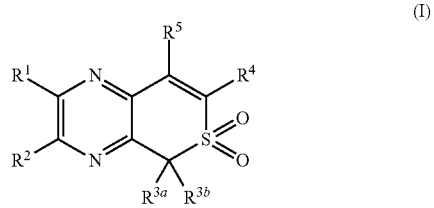

11 Claims, No Drawings

6,6-DIOXO-6-THIA-1, 4-DIAZA-NAPHTHALENES AS HERBICIDES

This application is a 371 of International Application No. PCT/GB2010/000892 filed May 6, 2010, which claims priority to GB 0908293.4 filed May 14, 2009, the contents of which are incorporated herein by reference.

The present invention relates to 6,6-dioxo-6-thia-1,4-diaza-naphthalene derivatives, to processes and intermediates for making these compounds, to herbicidal compositions comprising these compounds and to methods of using these compounds to control plant growth.

Certain 3,4-dihydro-2,2-dioxo-1H-2-benzothiopyranes are disclosed as herbicides in U.S. Pat. No. 4,904,300. Certain 7,8-dihydro-6,6-dioxo-5H-thiopyrano[4,3-b]pyridines are disclosed as herbicides in U.S. Pat. No. 4,824,474.

It has now surprisingly been found that 6,6-dioxo-6-thia-1,4-diaza-naphthalene derivatives have herbicidal properties.

The present invention therefore provides a compound of formula (I)

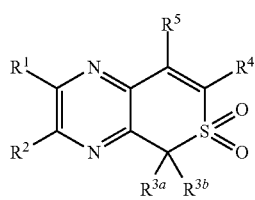

(I)

where $R^1$ and $R^2$ are independently hydrogen, halogen, cyano, $C_1$-$C_8$alkyl, $C_1$-$C_8$haloalkyl, hydroxy, $C_1$-$C_8$alkoxy-, thiol or $C_1$-$C_8$alkylthio-; $R^{3a}$ and $R^{3b}$ are independently hydrogen, halogen, cyano, $C_1$-$C_8$alkyl, $C_1$-$C_8$alkoxy-$C_1$-$C_4$alkyl-, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_3$-$C_{10}$cycloalkyl-$C_1$-$C_4$alkyl-, heterocyclyl, heterocyclyl-$C_1$-$C_4$alkyl-, or $C_1$-$C_8$alkoxycarbonyl-; or $R^{3a}$ and $R^{3b}$ together with the carbon atom they are attached to join to form a 3- to 10-membered carbocyclic ring or a 3- to 10-membered heterocyclic ring; $R^4$ is aryl or aryl substituted by one to five $R^6$, or heteroaryl or heteroaryl substituted by one to five $R^6$; $R^5$ is hydroxy or a group which can be metabolized to a hydroxy group; each $R^6$ is independently halogen, cyano, nitro, $C_1$-$C_8$alkyl, $C_1$-$C_8$alkoxy-$C_1$-$C_4$alkyl-, $C_1$-$C_8$haloalkyl, $C_1$-$C_8$haloalkoxy-$C_1$-$C_4$alkyl-, hydroxy, $C_1$-$C_8$alkoxy-, $C_1$-$C_8$haloalkoxy-, thiol, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, amino, N—$C_1$-$C_8$alkylcarbonylamino-, N—$C_1$-$C_8$alkyl-N—$C_1$-$C_8$alkylcarbonylamino-, N—$C_1$-$C_8$alkylsulfonylamino-, N—$C_1$-$C_8$alkyl-N—$C_1$-$C_8$alkylsulfonylamino-, aryl or aryl substituted by one to five $R^7$, heteroaryl or heteroaryl substituted by one to five $R^7$, aryloxy- or aryloxy-substituted by one to five $R^7$, heteroaryloxy- or heteroaryloxy-substituted by one to five $R^7$, arylthio- or arylthio-substituted by one to five $R^7$, or heteroarylthio- or heteroarylthio-substituted by one to five $R^7$; and each $R^7$ is independently halogen, cyano, nitro, $C_1$-$C_8$alkyl, $C_1$-$C_8$haloalkyl, $C_1$-$C_8$alkoxy- or $C_1$-$C_8$haloalkoxy-; or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds. Furthermore, it is possible that atropisomers are obtained in those cases where the rotation of the $R^4$ group is restricted, for example in those cases where the $R^4$ group has at least one ortho-substituent.

For example, a compound of formula (Ia), i.e. a compound of formula (I) where $R^5$ is hydroxy, can be drawn in two tautomeric forms.

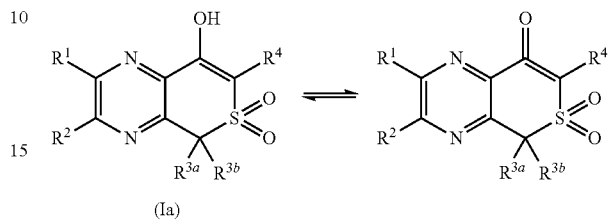

(Ia)

The compounds of the invention may contain one or more asymmetric carbon atoms, for example, at the —$CR^{3a}R^{3b}$— group, and may exist as enantiomers (or as pairs of diastereoisomers) or as mixtures of such.

Alkyl groups (either alone or as part of a larger group, such as alkoxy-, alkoxy-carbonyl-, alkylcarbonyl-) can be in the form of a straight or branched chain and are, for example, methyl, ethyl, propyl, prop-2-yl, butyl, but-2-yl, 2-methyl-prop-1-yl or 2-methyl-prop-2-yl. The alkyl groups are preferably $C_1$-$C_6$, more preferably $C_1$-$C_4$, most preferably $C_1$-$C_3$ alkyl groups.

Alkenyl groups (either alone or as part of a larger group, such as alkenyloxy-) can be in the form of straight or branched chains, and can be, where appropriate, of either the (E)- or (Z)-configuration. Examples are vinyl and allyl. The alkenyl groups are preferably $C_2$-$C_6$, more preferably $C_2$-$C_4$, most preferably $C_2$-$C_3$ alkenyl groups.

Alkynyl groups (either alone or as part of a larger group, such as alkynyloxy-) can be in the form of straight or branched chains. Examples are ethynyl and propargyl. The alkynyl groups are preferably $C_2$-$C_6$, more preferably $C_2$-$C_4$, most preferably $C_2$-$C_3$ alkynyl groups.

Halogen is fluorine, chlorine, bromine or iodine.

Haloalkyl groups (either alone or as part of a larger group, such as haloalkoxy- or haloalkylthio-) are alkyl groups which are substituted by one or more of the same or different halogen atoms and are, for example, difluoromethyl, trifluoromethyl, chlorodifluoromethyl or 2,2,2-trifluoro-ethyl.

Haloalkenyl groups are alkenyl groups which are substituted by one or more of the same or different halogen atoms and are, for example, 2,2-difluoro-vinyl or 1,2-dichloro-2-fluoro-vinyl.

Haloalkynyl groups are alkynyl groups which are substituted by one or more of the same or different halogen atoms and are, for example, 1-chloro-prop-2-ynyl.

Cycloalkyl groups and carbocyclic rings (either alone or as part of a larger group, such as cycloalkyl-alkyl-) can be in mono- or bi-cyclic form and are, for example, cyclopropyl, cyclobutyl, cyclohexyl and bicyclo[2.2.1]hept-2-yl. The cycloalkyl groups are preferably $C_3$-$C_8$, more preferably $C_3$-$C_6$ cycloalkyl groups.

Heterocyclyl groups and heterocyclic rings (either alone or as part of a larger group, such as heterocyclyl-alkyl-) are ring systems containing at least one heteroatom and can be in mono- or bi-cyclic form. Preferably, heterocyclyl groups will contain up to two heteroatoms which will preferably be chosen from nitrogen, oxygen and sulfur. Examples of heterocyclic groups include oxetanyl, thietanyl, azetidinyl and 7-oxabicyclo[2.2.1]hept-2-yl. Heterocyclyl groups containing a single oxygen atom as heteroatom are most preferred. The heterocyclyl groups are preferably 3- to 8-membered, more preferably 3- to 6-membered rings.

Aryl groups (either alone or as part of a larger group, such as aryloxy- or arylthio-) are aromatic ring systems which can be in mono-, bi- or tricyclic form. Examples of such rings include phenyl, naphthyl, anthracenyl, indenyl or phenanthrenyl. Preferred aryl groups are phenyl and naphthyl, phenyl being most preferred. Where an aryl moiety is substituted, the aryl moiety is preferably substituted by one to four substituents, most preferably by one to three substituents.

Heteroaryl groups (either alone or as part of a larger group, such as heteroaryloxy- or heteroarylthio-) are aromatic ring system containing at least one heteroatom and consisting either of a single ring or of two or more fused rings. Preferably, single rings will contain up to three heteroatoms which will preferably be chosen from nitrogen, oxygen and sulfur. Examples of monocyclic groups include pyridyl, pyridazinyl, pyrimidinyl, pyrazinyl, triazinyl, pyrrolyl, pyrazolyl, imidazolyl, triazolyl, tetrazolyl, furanyl, thiophenyl, oxazolyl, isoxazolyl, oxadiazolyl, thiazolyl, isothiazolyl and thiadiazolyl. Preferably, bicyclic systems will contain up to four heteroatoms which will preferably be chosen from nitrogen, oxygen and sulfur. Examples of bicyclic groups include quinolinyl, cinnolinyl, quinoxalinyl, indolyl, indazolyl, benzimidazolyl, benzothiophenyl and benzothiadiazolyl. Monocyclic heteroaryl groups are preferred, pyridyl being most preferred. Where a heteroaryl moiety is substituted, the heteroaryl moiety is preferably substituted by one to four substituents, most preferably by one to three substituents.

Metabolism means the conversion or breakdown of a substance from one form to another by a living organism, in particular in a plant (in planta).

Salts comprise a charged version of a compound of formula (I) and a counter ion of the opposite charge. The compounds of formula (I) can have a negative charge, for example, on an oxygen atom of a hydroxy group, if the hydroxy group is deprotonated with a base. Suitable bases include ammonia. Suitable cationic counter ions include, for example, alkali metals such as sodium or potassium, or alkaline earth metals such as magnesium and calcium, or quaternary ammonium bases such as ammonium and tetramethylammonium. Alternatively, the compounds of formula (I) can have a positive charge, for example, on the nitrogen atom in a nitrogen-containing heteroaryl group, if the nitrogen atom is quaternised by protonation with an organic or inorganic acid, or if the nitrogen atom is quaternised by alkylation for example with a methyl group, or if the nitrogen atom is quaternised by amination. Suitable anionic counter ions include, for example, the dissociated acid anion or a simple anion such as hydroxide, chloride or bromide.

The compounds of formula (I) according to the invention also include hydrates which may be formed, for example, during salt formation.

N-oxides are compounds of formula (I) where a nitrogen atom has been oxidised. In particular, N-oxides are compounds of formula (I) where the nitrogen atom in a nitrogen-containing heteroaryl group has been oxidised.

Preferred values $R^1$, $R^2$, $R^{3a}$, $R^{3b}$, $R^4$, $R^5$, $R^6$, $R^7$, $R^8$ and $R^9$ are, in any combination, as set out below.

Preferably $R^1$ is hydrogen, halogen or $C_1$-$C_8$alkyl, more preferably hydrogen, chloro or methyl, most preferably hydrogen.

Preferably $R^2$ is hydrogen, halogen or $C_1$-$C_8$alkyl, more preferably hydrogen, chloro or methyl, most preferably hydrogen.

Preferably $R^{3a}$ is hydrogen, halogen, $C_1$-$C_8$alkyl, $C_1$-$C_8$haloalkyl or $C_2$-$C_8$alkynyl, more preferably hydrogen. Examples of preferred $R^{3a}$ groups include hydrogen, fluoro, methyl, ethyl, 2,2-difluoro-ethyl and propargyl.

Preferably $R^{3b}$ is hydrogen, halogen, $C_1$-$C_8$alkyl, $C_1$-$C_8$haloalkyl or $C_2$-$C_8$alkynyl, more preferably hydrogen. Examples of preferred $R^{3b}$ groups include hydrogen, fluoro, methyl, ethyl, 2,2-difluoro-ethyl and propargyl.

In one embodiment both $R^{3a}$ and $R^{3b}$ are hydrogen.
In one embodiment both $R^{3a}$ and $R^{3b}$ are fluoro.
In one embodiment both $R^{3a}$ is fluoro and $R^{3b}$ is hydrogen.
In one embodiment $R^{3a}$ is methyl and $R^{3b}$ is hydrogen.
In one embodiment both $R^{3a}$ and $R^{3b}$ are methyl.
In one embodiment $R^{3a}$ is 2,2-difluoro-ethyl and $R^{3b}$ is hydrogen.
In one embodiment $R^{3a}$ is 2,2-difluoro-ethyl and $R^{3b}$ is methyl.
In one embodiment $R^{3a}$ and $R^{3b}$ together with the carbon atom they are attached to join to form cyclopropyl.

Preferably $R^4$ is phenyl or phenyl substituted by one to five $R^6$, or heteroaryl or heteroaryl substituted by one to five $R^6$ (where heteroaryl is pyridyl, pyrimidinyl, pyrazolyl, triazolyl, thiophenyl, isoxazolyl, oxadiazolyl or thiazolyl); more preferably phenyl or phenyl substituted by one to five $R^6$, or pyridyl or pyridyl substituted by one to five $R^6$; most preferably phenyl or phenyl substituted by one to five $R^6$.

In one embodiment $R^4$ is 2,5-bis-(trifluoromethyl)-phenyl-.

In one embodiment $R^4$ is 3-bromo-2-chloro-6-fluoro-phenyl-.
In one embodiment $R^4$ is 2-bromo-5-chloro-phenyl-.
In one embodiment $R^4$ is 2-bromo-phenyl-.
In one embodiment $R^4$ is 4-bromo-2-trifluoromethyl-phenyl-.
In one embodiment $R^4$ is 2-chloro-3,6-difluoro-phenyl-.
In one embodiment $R^4$ is 2-chloro-6-fluoro-3-trifluoromethyl-phenyl-.
In one embodiment $R^4$ is 4-chloro-2-methylsulfonyl-phenyl-.
In one embodiment $R^4$ is 2-chloro-5-trifluoromethyl-phenyl-.
In one embodiment $R^4$ is 2-chloro-6-trifluoromethyl-phenyl-.
In one embodiment $R^4$ is 4-chloro-2-trifluoromethyl-phenyl-.
In one embodiment $R^4$ is 5-chloro-2-trifluoromethyl-phenyl-.
In one embodiment $R^4$ is 2,3-dichloro-6-fluoro-phenyl-.
In one embodiment $R^4$ is 2,6-dichloro-phenyl-.
In one embodiment $R^4$ is 2,6-dichloro-3-trifluoromethyl-phenyl-.
In one embodiment $R^4$ is 3,5-difluoro-2-trifluoromethyl-phenyl-.
In one embodiment $R^4$ is 2-ethyl-4-(4'-chloro-phenyl)-phenyl-.
In one embodiment $R^4$ is 2,3,6-trichloro-phenyl-.
In one embodiment $R^4$ is 2-trifluoromethyl-phenyl-.
In one embodiment $R^4$ is 2,4,6-trimethyl-phenyl-.

Preferably $R^5$ is hydroxy or $R^8$-oxy-, where $R^8$ is $C_1$-$C_8$alkyl-, $C_2$-$C_8$alkenyl-, $C_2$-$C_8$alkynyl-, aryl-$C_1$-$C_4$alkyl- or aryl-$C_1$-$C_4$alkyl- where the aryl moiety is substituted by one to five $R^9$, $C_1$-$C_8$alkylcarbonyl-, $C_1$-$C_8$alkoxycarbonyl-, $C_1$-$C_8$alkylthiocarbonyl- or $C_1$-$C_8$alkylsulfonyl-; where each $R^9$ is independently halogen, cyano, nitro, $C_1$-$C_8$alkyl, $C_1$-$C_8$haloalkyl, $C_1$-$C_8$alkoxy- or $C_1$-$C_8$haloalkoxy-. Examples of preferred $R^5$ groups include hydroxy, methoxy-, allyloxy-, propargyloxy-, benzyloxy-, prop-2-ylcarbonyloxy-, 2-methyl-prop-2-ylcarbonyloxy-, ethoxycarbonyloxy-, ethylthiocarbonyloxy- and methylsulfonyloxy-.

In one embodiment $R^5$ is hydroxy.

In one embodiment $R^5$ is prop-2-ylcarbonyloxy- or 2-methyl-prop-2-ylcarbonyloxy-.

Preferably each $R^6$ is independently halogen, cyano, nitro, $C_1$-$C_8$alkyl, $C_1$-$C_8$haloalkyl, $C_1$-$C_8$alkoxy-, $C_1$-$C_8$haloalkoxy-, $C_1$-$C_8$alkylthio-, or $C_1$-$C_8$haloalkylthio-, more preferably halogen, $C_1$-$C_8$alkyl, $C_1$-$C_8$haloalkyl, $C_1$-$C_8$alkoxy- or $C_1$-$C_8$haloalkoxy-. Examples of preferred $R^6$ groups include bromo, chloro, fluoro, methyl, ethyl, trifluoromethyl, methoxy and trifluoromethoxy.

Examples of preferred $R^7$ groups include bromo, chloro, fluoro, methyl, ethyl, trifluoromethyl, methoxy and trifluoromethoxy.

Examples of preferred $R^8$ groups include methyl, allyl, propargyl, benzyl, prop-2-ylcarbonyl-, 2-methyl-prop-2-ylcarbonyl-, ethoxycarbonyl-, ethylthiocarbonyl- and methylsulfonyl-.

Examples of preferred $R^9$ groups include bromo, chloro, fluoro, methyl, ethyl, trifluoromethyl, methoxy and trifluoromethoxy.

Certain intermediates are novel and thus form another embodiment of this invention. Thus, one embodiment is a compound of formula (6)

(6)

where $R^1$, $R^2$ and $R^4$ are as defined for a compound of formula (I) and $R^{10}$ is $C_1$-$C_8$alkyl; or a salt or N-oxide thereof. The preferences for $R^1$, $R^2$ and $R^4$ are the same as defined for a compound of formula (I). Preferably $R^{10}$ is methyl or ethyl.

A further embodiment is a compound of formula (9)

(9)

where $R^1$, $R^2$, $R^{3a}$, $R^{3b}$ and $R^4$ are as defined for a compound of formula (I) and $R^{10}$ is $C_1$-$C_8$alkyl; or a salt or N-oxide thereof. The preferences for $R^1$, $R^2$ and $R^4$ are the same as defined for a compound of formula (I). Preferably $R^{10}$ is methyl or ethyl.

Compounds of formula (9a) are compounds of formula (9) where $R^{3a}$ and $R^{3b}$ are both hydrogen. Therefore a still further embodiment is a compound of formula (9a)

(9a)

where $R^1$, $R^2$ and $R^4$ are as defined for a compound of formula (I) and $R^{10}$ is $C_1$-$C_8$alkyl; or a salt or N-oxide thereof. The preferences for $R^1$, $R^2$ and $R^4$ are the same as defined for a compound of formula (I). Preferably $R^{10}$ is methyl or ethyl.

A further embodiment is a compound of formula (10)

(10)

where $R^1$, $R^2$ and $R^4$ are as defined for a compound of formula (I); or a salt or N-oxide thereof. The preferences for $R^1$, $R^2$ and $R^4$ are the same as defined for a compound of formula (I).

The compounds in Tables 1 to 8 below illustrate the compounds of the invention.

TABLE 1

In Table X below, when X = 1, Table 1 provides 20 compounds of formula (Ib), where $R^4$ has the values listed in Table 1.
Compounds of formula (Ib) are compounds of formula (I) where $R^1$, $R^2$, $R^{3a}$ and $R^{3b}$ are each hydrogen and $R^5$ is hydroxy.

(Ib)

TABLE 2

In Table X below, when X = 2, Table 2 provides 20 compounds of formula (Ic), where $R^4$ has the values listed in Table 2.
Compounds of formula (Ic) are compounds of formula (I) where $R^1$, $R^2$ and $R^{3a}$ are each hydrogen; $R^{3b}$ is methyl; and $R^5$ is hydroxy.

(Ic)

TABLE 3

In Table X below, when X = 3, Table 3 provides 20 compounds of formula (Id), where $R^4$ has the values listed in Table 3. Compounds of formula (Id) are compounds of formula (I) where $R^1$ and $R^2$ are each hydrogen; $R^{3a}$ and $R^{3b}$ are each methyl; and $R^5$ is hydroxy.

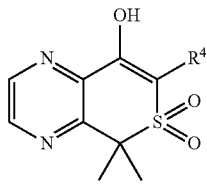

(Id)

TABLE 4

In Table X below, when X = 4, Table 4 provides 20 compounds of formula (Ie), where $R^4$ has the values listed in Table 4. Compounds of formula (Ie) are compounds of formula (I) where $R^1$, $R^2$ and $R^{3a}$ are each hydrogen; $R^{3b}$ is ethyl; and $R^5$ is hydroxy.

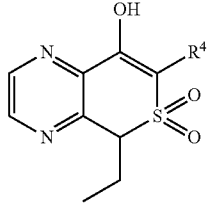

(Ie)

TABLE 5

In Table X below, when X = 5, Table 5 provides 20 compounds of formula (If), where $R^4$ has the values listed in Table 5. Compounds of formula (If) are compounds of formula (I) where $R^1$ and $R^2$ are each hydrogen; $R^{3a}$ is methyl; $R^{3b}$ is propargyl; and $R^5$ is hydroxy.

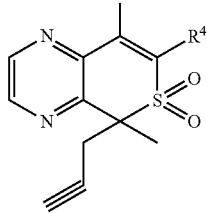

(If)

TABLE 6

In Table X below, when X = 6, Table 6 provides 20 compounds of formula (Ig), where $R^4$ has the vlaues listed in Table 6. Compounds of formula (Ig) are compounds of formula (I) where $R^1$, $R^2$ and $R^{3a}$ are each hydrogen; $R^{3b}$ is propargyl; and $R^5$ is hydroxy.

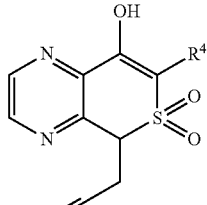

(Ig)

TABLE 7

In Table X below, when X = 7, Table 7 provides 20 compounds of formula (Ih), where $R^4$ has the values listed in Table 7. Compounds of formula (Ih) are compounds of formula (I) where $R^1$, $R^2$ and $R^{3a}$ are each hydrogen; $R^{3b}$ is $F_2HC-H_2C-$; and $R^5$ is hydroxy.

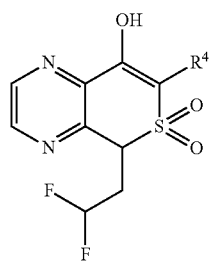

(Ih)

TABLE 8

In Table X below, when X = 8, Table 8 provides 20 compounds of formula (Ii), where $R^4$ has the values listed in Table 8. Compounds of formula (Ii) are compounds of formula (I) where $R^1$ and $R^2$ are each hydrogen; $R^{3a}$ and $R^{3b}$ and the carbon atom to which they are both joined form cyclopropyl; and $R^5$ is hydroxy.

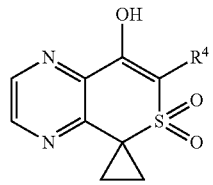

(Ii)

TABLE X

| Comp. No. | $R^4$ |
|---|---|
| X.01 | 2,5-bis-(trifluoromethyl)-phenyl- |
| X.02 | 3-bromo-2-chloro-6-fluoro-phenyl- |
| X.03 | 2-bromo-5-chloro-phenyl- |
| X.04 | 2-bromo-phenyl- |
| X.05 | 4-bromo-2-trifluoromethyl-phenyl- |
| X.06 | 2-chloro-3,6-difluoro-phenyl- |
| X.07 | 2-chloro-6-fluoro-3-trifluoromethyl-phenyl- |
| X.08 | 4-chloro-2-methylsulfonyl-phenyl- |
| X.09 | 2-chloro-5-trifluoromethyl-phenyl- |
| X.10 | 2-chloro-6-trifluoromethyl-phenyl- |
| X.11 | 4-chloro-2-trifluoromethyl-phenyl- |
| X.12 | 5-chloro-2-trifluoromethyl-phenyl- |
| X.13 | 2,3-dichloro-6-fluoro-phenyl- |
| X.14 | 2,6-dichloro-phenyl- |
| X.15 | 2,6-dichloro-3-trifluoromethyl-phenyl- |
| X.16 | 3,5-difluoro-2-trifluoromethyl-phenyl- |
| X.17 | 2-ethyl-4-(4'-chloro-phenyl)-phenyl- |
| X.18 | 2,3,6-trichloro-phenyl- |
| X.19 | 2-trifluoromethyl-phenyl- |
| X.20 | 2,4,6-trimethyl-phenyl- |

The compounds of the invention may be made by a variety of methods, for example by the methods described in Schemes 1 to 6.

Scheme 1

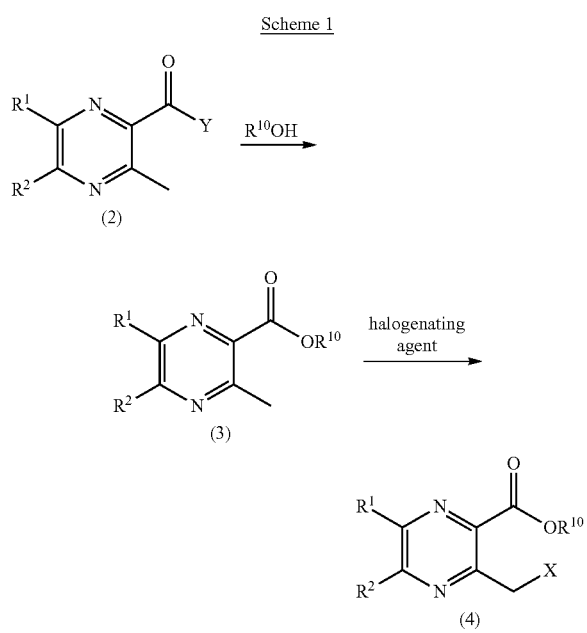

tives of formula (2) are commercially available or can be made by methods known to a person skilled in the art.

2) A carboxylic ester of formula (4) where $R^1$ and $R^2$ are as defined for a compound of formula (I) and $R^{10}$ is as defined in 1) can be made by reacting a carboxylic ester of formula (3) as defined in 1) with a halogenating agent, such as a halogen of formula $X_2$ where X is chlorine or bromine, in the presence of light, or a N-halosuccinimide of formula

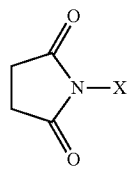

where X is chlorine, bromine or iodine, in the presence of a radical initiator, such as 2,2'-azobis(2-methylpropionitrile) ("AIBN"), in a solvent, such as carbon tetrachloride, and optionally in the presence of a light source, such as a 500 watt tungsten halogen lamp, preferably at the reflux temperature of the solvent.

Scheme 2

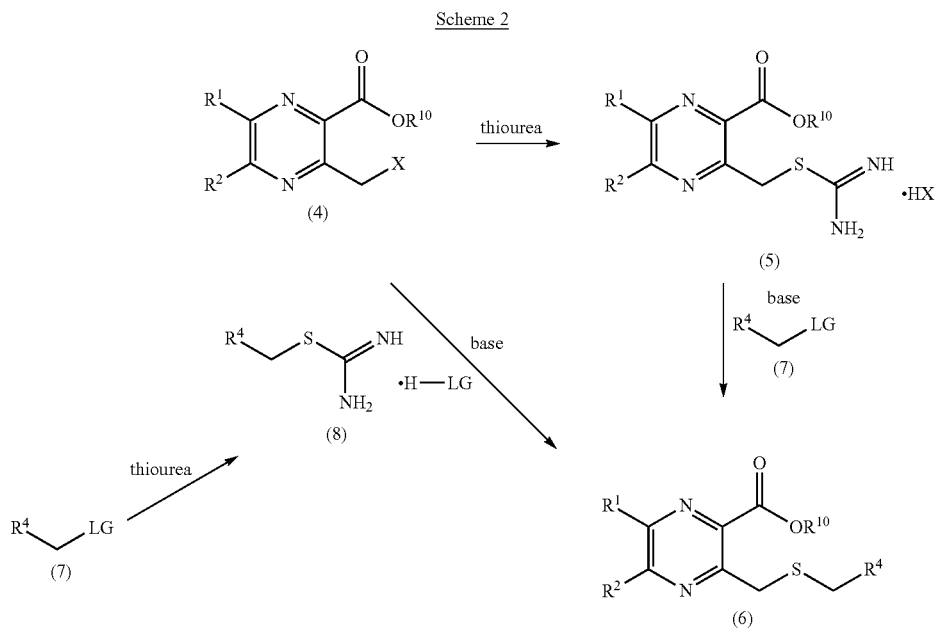

1) A carboxylic ester of formula (3) where $R^1$ and $R^2$ are as defined for a compound of formula (I) and $R^{10}$ is $C_1$-$C_8$alkyl can be made by reacting an acid derivative of formula (2), where $R^1$ and $R^2$ are as defined for a compound of formula (I) and Y is a halogen atom or a hydroxy group, with an alcohol $R^{10}$OH where $R^{10}$ is $C_1$-$C_8$alkyl, as shown in Scheme 1. When Y is a halogen atom, such as a chloro atom, the reaction can conveniently be carried out in the presence of a base, such as triethylamine or pyridine, in a solvent, such as acetonitrile or dichloromethane, optionally using microwave heating. When Y is a hydroxy group, the reaction can conveniently be carried out using a coupling method as reviewed, for example, in Tetrahedron (2005), 61(46), 10827-10852. Acid deriva- 3) A thiouronium salt of formula (5) where $R^1$ and $R^2$ are as defined for a compound of formula (I) and $R^{10}$ is as defined in 1) can be made by reacting a carboxylic ester of formula (4) as defined in 2) with thiourea in a solvent, such as tetrahydrofuran, 2-butanone or dichloromethane, optionally using microwave heating, as shown in Scheme 2.

4) A thioether of formula (6) where $R^1$, $R^2$ and $R^4$ are as defined for a compound of formula (I) and $R^{10}$ is as defined in 1) can be made by reacting a thiouronium salt of formula (5) as defined in 3) with a benzylic compound of formula (7) where $R^4$ is as defined for a compound of formula (I) and LG is a leaving group, for example a halide [such as chloride, bromide or iodide], tosylate, mesylate or triflate, in the presence of a base [such as potassium carbonate] in a solvent [such as acetonitrile or N,N-dimethylformamide] and optionally using microwave heating. Benzylic compounds of formula (7) are commercially available or can be made by methods known to a person skilled in the art.

5) Alternatively, a thioether of formula (6) as defined in 4) can be made by reacting a carboxylic ester of formula (4) as defined in 2) with a thiouronium salt of formula (8) where $R^4$ is as defined for a compound of formula (I), in the presence of a base, such as potassium carbonate, in a solvent, such as acetonitrile or N,N-dimethylformamide, optionally using microwave heating. Thiouronium salts of formula (8) can be made by reacting a benzylic compound of formula (7) as defined in 4) with thiourea in a solvent, such as tetrahydrofuran, 2-butanone or dichloromethane, optionally using microwave heating. Compounds of formula (7) are commercially available or can be made by methods known to the person skilled in the art.

Scheme 3

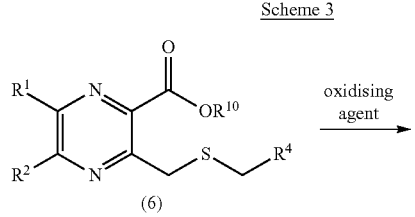

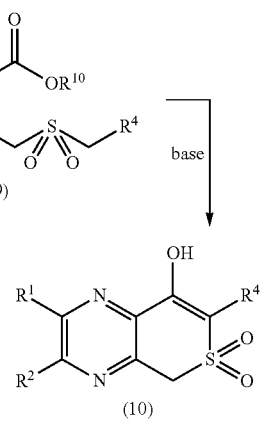

6) A sulfone of formula (9) where $R^1$, $R^2$ and $R^4$ are as defined for a compound of formula (I) and $R^{10}$ is as defined in 1) can be made by reacting a thioether of formula (6) as defined in 4) with an oxidising agent, such as 3-chloroperoxybenzoic acid ("MCPBA"), in a solvent, such as dichloromethane, preferably at ambient temperature as shown in Scheme 3.

7) An 8-hydroxy naphthalene of formula (10) where $R^1$, $R^2$ and $R^4$ are as defined for a compound of formula (I) can be made by reacting a compound of formula (9) as defined in 6) with a base, such as potassium carbonate, in a solvent, such as acetonitrile or N,N-dimethylformamide, optionally using microwave heating.

Scheme 4

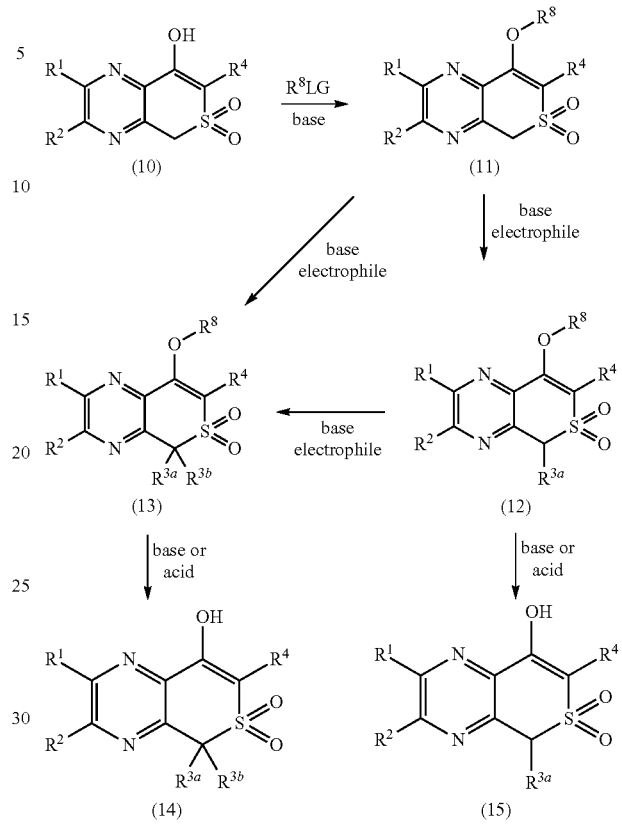

8) An 8-substituted naphthalene of formula (11) where $R^1$, $R^2$ and $R^4$ are as defined for a compound of formula (I) and $R^8$ is as defined for a compound of formula (I) can be made by reacting an 8-hydroxy naphthalene of formula (10) as defined in 7) with a compound of formula $R^8LG$ where $R^8$ is as defined for a compound of formula (I) and LG is as defined in 4) in the presence of a base, such as triethylamine, pyridine or potassium tert-butoxide, in a solvent, such as dichloromethane or tetrahydrofuran, optionally using microwave heating, as shown in Scheme 4. Where $R^8$ is methyl, methyl iodide can conveniently be used as reagent. When $R^8$ is allyl, propargyl or benzyl, the corresponding bromide, such as benzyl bromide, can conveniently be used as reagent. When $R^8$ is prop-2-ylcarbonyl-, 2-methyl-prop-2-ylcarbonyl-, ethoxycarbonyl-, ethylthiocarbonyl- or methylsulfonyl-, the corresponding chloride, such as methanesulfonyl chloride, can conveniently be used as reagent.

9) A 5-substituted naphthalene of formula (12) where $R^1$, $R^2$, $R^{3a}$ and $R^4$ are as defined for a compound of formula (I) and $R^8$ is as defined in 8) can be made by reacting an 8-substituted naphthalene of formula (11) as defined in 8) first with a base, such as lithium diisopropylamine, 1,8-diazabicyclo[5.4.0]undec-7-ene or potassium tert-butoxide, and then with an electrophile, such as an alkylating agent, a halogenating agent or a cyanating agent, in a solvent, such as tetrahydrofuran, optionally using microwave heating. Suitable alkylating agents are, for example, alkyl halides, such as methyl iodide, for making a compound where $R^{3a}$ is $C_1$-$C_8$ alkyl, in particular methyl. Suitable halogenating agents are, for example, 4-iodotoluene difluoride (CAS RN 371-11-9) or N-fluorobenzenesulfonimide ("NFSI"), N-chlorosuccinimide ("NCS"), N-bromosuccinimide ("NBS"), and N-iodosuccinimide ("NIS"), for making a compound where $R^{3a}$ is F, Cl, Br, or I, respectively. Suitable cyanating agents are, for example, cyanogen bromide, 1-cyanobenzotriazole, phenyl cyanate ("PhOCN") or tosyl cyanide for making a compound where $R^{3a}$ is cyano.

10) A 5,5-disubstituted naphthalene of formula (13) where $R^1$, $R^2$, $R^{3a}$, $R^{3b}$ and $R^4$ are as defined for a compound of formula (I) and $R^8$ is as defined in 8) can be made by reacting an 8-substituted naphthalene of formula (11) as defined in 8) typically with two equivalents of base and two equivalents of electrophile as defined under 9) applied simultaneously or successively. Where $R^{3a}$ and $R^{3b}$ are the same it is preferred to carry out the reactions simultaneously, without isolation of the intermediate. Where $R^{3a}$ and $R^{3b}$ are different it is preferred to carry out the reactions successively, optionally isolating the intermediate.

11) A naphthalene of formula (14) where $R^1$, $R^2$, $R^{3a}$, $R^{3b}$ and $R^4$ are as defined for a compound of formula (I) or a naphthalene of formula (15) where $R^1$, $R^2$, $R^{3a}$ and $R^4$ are as defined for a compound of formula (I) can be made by reacting a 5,5-disubstituted naphthalene of formula (13) as defined in 10) or a 5-substituted naphthalene of formula (12) as defined in 9), with water, in the presence of a base, such as lithium hydroxide, in a solvent, such as tetrahydrofuran, or in the presence of an acid, such as concentrated sulfuric acid, with or without a solvent, optionally using microwave heating.

defined in 12) with a base, such as potassium carbonate, in a solvent, such as acetonitrile or N,N-dimethylformamide, optionally using microwave heating. A 5-substituted naphthalene of formula (15) can also be prepared in 'one-pot' using conditions described in 12) from a sulfone of formula (9).

14) A sulfone of formula (17) where $R^1$, $R^2$, $R^{3a}$, $R^{3b}$ and $R^4$ are as defined for a compound of formula (I) and $R^{10}$ is as defined in 1) and where $R^{3a}$ and $R^{3b}$ are the same as each other, can be made by reacting a sulfone of formula (9) as defined in 6) with typically two equivalents of base and two equivalents of electrophile as defined in 9) in a solvent as defined and described in 12).

15) A sulfone of formula (17) where $R^1$, $R^2$, $R^{3a}$, $R^{3b}$ and $R^4$ are as defined for a compound of formula (I) and $R^{10}$ is as defined in 1) and where $R^{3a}$ and $R^{3b}$ are different from each other, can be prepared by reacting a sulfone of formula (16) as defined in 12) with a base such as potassium tert-pentoxide in a solvent, such as N,N-dimethylformamide, and then with an electrophile as defined in 9). A sulfone of formula (17) can also be prepared by reacting a sulfone of formula (9) as defined in 6) with typically two equivalents of base and successively two different electrophiles, optionally isolating the intermediate.

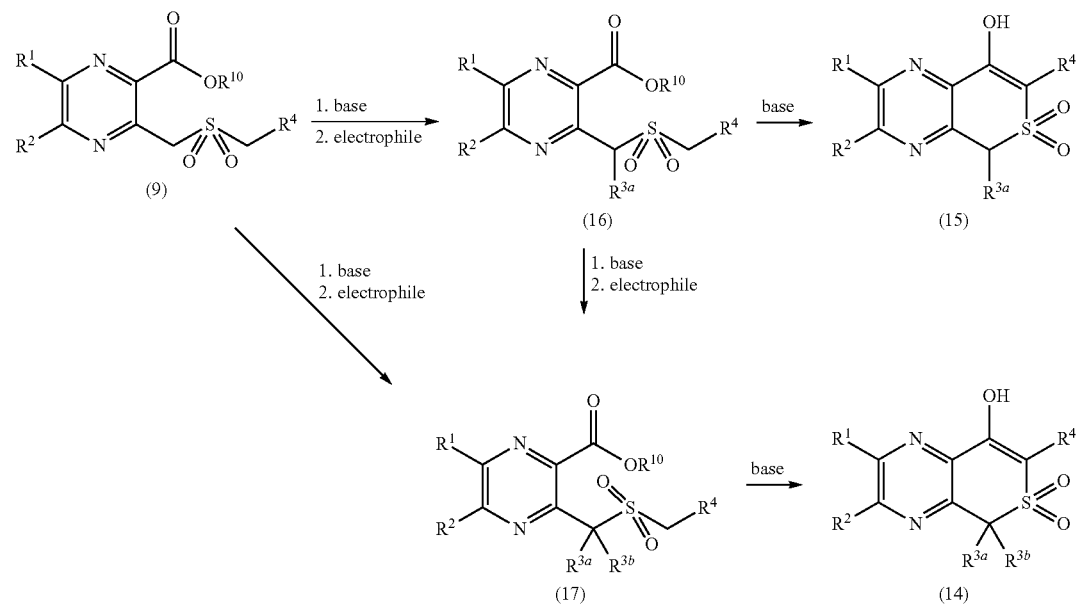

Scheme 5

12) A sulfone of formula (16) where $R^1$, $R^2$, $R^{3a}$ and $R^4$ are as defined for a compound of formula (I) and $R^{10}$ is as defined in 1) can be made by reacting a sulfone of formula (9) as defined in 6) first with a base, such as lithium diisopropylamine, potassium tert-pentoxide or potassium tert-butoxide, and then with an electrophile, as defined in 9), as shown in Scheme 5.

13) A 5-substituted naphthalene of formula (15) as defined in 11) can be made by reacting a compound of formula (16) as 16) A 5,5-disubstituted naphthalene of formula (14) where $R^1$, $R^2$, $R^{3a}$, $R^{3b}$ and $R^4$ are as defined for a compound of formula (I) can be prepared by reacting a compound of formula (17) as defined in 15) with a base, such as potassium carbonate, in a solvent, such as acetonitrile or N,N-dimethylformamide, optionally using microwave heating. A 5,5-disubstituted naphthalene of formula (14) can also be prepared in 'one-pot' using conditions described in 12), 14) and 15) from a sulfone of formula (9).

Scheme 6

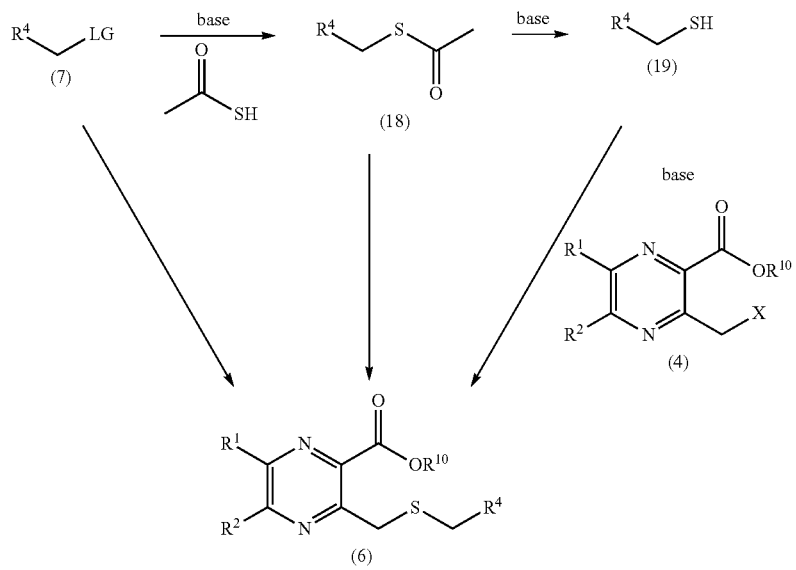

17) A thioacetate of formula (18) where $R^4$ is as defined for a compound of formula (I) can be prepared by reacting a benzylic compound of formula (7) as defined in 4) with a base [such as potassium carbonate] and thioacetic acid or an inorganic salt of thioacetic acid [such as potassium thioacetate], in a solvent [such as acetone or an alcohol] and optionally using heating.

18) A thiol of formula (19) where $R^4$ is as defined for a compound of formula (I) can be prepared by reacting a compound of formula (18) as defined in 17) with a base [such as potassium carbonate], in a solvent [such as acetone or an alcohol] and optionally using heating. Alternatively a thiol of formula (19) can be prepared in one pot from a compound of formula (7) as described in Tetrahedron Letters 47, 8255, 2006.

19) A thioether of formula (6) as defined in 4) can be prepared by reacting a compound of formula (19) as defined in 18) with a carboxylic ester of formula (4) as defined in 2) with a base [such as potassium carbonate], in a solvent [such as acetone or an alcohol] and optionally using heating. Alternatively a thioether of formula (6) can be prepared in 'one pot' from a compound of formula (7) or a compound of formula (18) using sequential procedures as outlined in 17) and 18) without isolating the compound (18) or (19).

The compounds of formula (I) according to the invention can be used as herbicides in unmodified form, as obtained in the synthesis, but they are generally formulated into herbicidal compositions in various ways using formulation adjuvants, such as carriers, solvents and surface-active substances. The formulations can be in various physical forms, for example in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO Specifications for Plant Protection Products, 5th Edition, 1999. Such formulations can either be used directly or they are diluted prior to use. The dilutions can be made, for example, with water, liquid fertilisers, micronutrients, biological organisms, oil or solvents.

The formulations can be prepared for example, by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof. The active ingredients can also be contained in very fine microcapsules consisting of a polymer. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art in this connection. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl, ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like. Water is generally the carrier of choice for diluting the concentrates. Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances, as described, for example, in CFR 180.1001. (c) & (d).

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecyl-benzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in "McCutcheon's Detergents and Emulsifiers Annual" MC Publishing Corp., Ridgewood N.J., 1981.

Further adjuvants that can usually be used in pesticidal formulations include crystallisation inhibitors, viscosity modifiers, suspending agents, dyes, anti-oxidants, foaming agents, light absorbers, mixing auxiliaries, antifoams, complexing agents, neutralizing or pH-modifying substances and buffers, corrosion inhibitors, fragrances, wetting agents, take-up enhancers, micronutrients, plasticisers, glidants, lubricants, dispersants, thickeners, antifreezes, microbicides, and also liquid and solid fertilizers.

The compositions according to the invention can additionally include an additive comprising an oil of vegetable or animal origin, a mineral oil, alkyl esters of such oils or mixtures of such oils and oil derivatives. The amount of oil additive in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being of importance. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combination with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltriloxanes which are commercially available e.g. as Silwet L-77®, and also perfluorinated surfactants. The concentration of the surface-active substances in relation to the total additive is generally from 1 to 30% by weight. Examples of oil additives consisting of mixtures of oil or mineral oils or derivatives thereof with surfactants are Edenor ME SU®, Turbocharge® (Syngenta AG, CH) or ActipronC (BP Oil UK Limited, GB).

If desired, it is also possible for the mentioned surface-active substances to be used in the formulations on their own, that is to say without oil additives.

Furthermore, the addition of an organic solvent to the oil additive/surfactant mixture may contribute to an additional enhancement of action. Suitable solvents are, for example, Solvesso® (ESSO) or Aromatic Solvent® (Exxon Corporation). The concentration of such solvents can be from 10 to 80% by weight of the total weight. Oil additives that are present in admixture with solvents are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada).

In addition to the oil additives listed above, for the purpose of enhancing the action of the compositions according to the invention it is also possible for formulations of alkyl-pyrrolidones (e.g. Agrimax®) to be added to the spray mixture. Formulations of synthetic lattices, e.g. polyacrylamide, polyvinyl compounds or poly-1-p-menthene (e.g. Bond®, Courier® or Emerald®) may also be used. It is also possible for solutions that contain propionic acid, for example Eurogkem Pen-e-trate®, to be added to the spray mixture as action-enhancing agent.

The herbicidal compositions generally comprise from 0.1 to 99% by weight, especially from 0.1 to 95% by weight, compounds of formula (I) and from 1 to 99.9% by weight of a formulation adjuvant which preferably includes from 0 to 25% by weight of a surface-active substance. Whereas commercial products will preferably be formulated as concentrates, the end user will normally employ dilute formulations.

The rates of application of compounds of formula (I) may vary within wide limits and depend on the nature of the soil, the method of application (pre- or post-emergence; seed dressing; application to the seed furrow; no tillage application etc.), the crop plant, the grass or weed to be controlled, the prevailing climatic conditions, and other factors governed by the method of application, the time of application and the target crop. The compounds of formula (I) according to the invention are generally applied at a rate of from 10 to 2000 g/ha, especially from 50 to 1000 g/ha.

Preferred formulations have especially the following compositions (%=percent by weight):
Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%
The following Examples further illustrate, but do not limit, the invention.

Formulation Examples for Herbicides of Formula (I)
(%=Percent by Weight)

| F1. Emulsifiable concentrates | | | | |
|---|---|---|---|---|
| | a) | b) | c) | d) |
| active ingredient | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be obtained from such concentrates by dilution with water.

| F2. Solutions | | | | |
|---|---|---|---|---|
| | a) | b) | c) | d) |
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for use in the form of microdrops.

| F3. Wettable powders | | | | |
|---|---|---|---|---|
| | a) | b) | c) | d) |
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| F4. Coated granules | | | |
|---|---|---|---|
| | a) | b) | c) |
| active ingredient | 0.1% | 5% | 15% |
| highly dispersed silicic acid | 0.9% | 2% | 2% |
| [inorganic carrier (diameter 0.1-1 mm) for example $CaCO_3$ or $SiO_2$] | 99.0% | 93% | 83% |

The active ingredient is dissolved in methylene chloride and applied to the carrier by spraying, and the solvent is then evaporated off in vacuo.

| F5. Coated granules | | | |
|---|---|---|---|
| | a) | b) | c) |
| active ingredient | 0.1% | 5% | 15% |
| polyethylene glycol MW 200 | 1.0% | 2% | 3% |

F5. Coated granules

|  | a) | b) | c) |
|---|---|---|---|
| highly dispersed silicic acid | 0.9% | 1% | 2% |
| [inorganic carrier (diameter 0.1-1 mm) for example CaCO$_3$ or SiO$_2$] | 98.0% | 92% | 80% |

The finely ground active ingredient is uniformly applied, in a mixer, to the carrier moistened with polyethylene glycol. Non-dusty coated granules are obtained in this manner.

F6. Extruder granules

|  | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

F7. Dusts

|  | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

F8. Suspension concentrates

|  | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

The present invention further relates to a method of controlling plants which comprises applying to the plants or to the locus thereof a herbicidally effective amount of a compound of formula (I).

The invention also relates to a method of inhibiting plant growth which comprises applying to the plants or to the locus thereof a herbicidally effective amount of a compound of formula (I).

The invention also relates to a method of selectively controlling grasses and weeds in crops of useful plants which comprises applying to the useful plants or locus thereof or to the area of cultivation a herbicidally effective amount of a compound of formula (I).

Compounds of formula (I), formulations and/or mixtures containing the same may also be used on turf, pasture, rangeland, rights of way etc. In particular they may be used on golf-courses, lawns, parks, sports-fields, race-courses and the like.

The term "herbicide" as used herein means a compound that controls or modifies the growth of plants. The term "herbicidally effective amount" means the quantity of such a compound or combination of such compounds that is capable of producing a controlling or modifying effect on the growth of plants. Controlling or modifying effects include all deviation from natural development, for example: killing, retardation, leaf burn, albinism, dwarfing and the like. The term "plants" refers to all physical parts of a plant, including seeds, seedlings, saplings, roots, tubers, stems, stalks, foliage, and fruits. The term "locus" is intended to include soil, seeds, and seedlings, as well as established vegetation.

Crops of useful plants in which the composition according to the invention can be used include perennial crops, such as citrus fruit, grapevines, nuts, oil palms, olives, pome fruit, stone fruit and rubber, and annual arable crops, such as cereals, for example barley and wheat, cotton, oilseed rape, maize, rice, soy beans, sugar beet, sugar cane, sunflowers, ornamentals and vegetables, especially cereals, maize and soy beans.

The grasses and weeds to be controlled may be both monocotyledonous species, for example *Agrostis*, *Alopecurus*, *Avena*, *Bromus*, *Cyperus*, *Digitaria*, *Echinochloa*, *Lolium*, *Monochoria*, *Rottboellia*, *Sagittaria*, *Scirpus*, *Setaria*, *Sida* and *Sorghum*, and dicotyledonous species, for example *Abutilon*, *Amaranthus*, *Chenopodium*, *Chrysanthemum*, *Galium*, *Ipomoea*, *Nasturtium*, *Sinapis*, *Solanum*, *Stellaria*, *Veronica*, *Viola* and *Xanthium*.

Crops are to be understood as also including those crops which have been rendered tolerant to herbicides or classes of herbicides (e.g. auxins or ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesize such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), YieldGard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

Areas under cultivation include land on which the crop plants are already growing and land intended for cultivation with those crop plants. The compounds of the invention can be applied before weeds emerge (pre-emergence application) or after weeds emerge (post-emergence application), and are particularly effective when applied post-emergence.

The compounds of formula (I) according to the invention can also be used in combination with one or more further herbicides. The combinations may well lead to synergistic effects. In particular, the following mixtures of the compound of formula (I) are important, where numbers given in brackets after compound names are often the corresponding reference numbers given in The Pesticide Manual, 13th Edition (BCPC), 2003:

Mixtures of a compound of formula (I) with a synthetic auxin (e.g. a compound of formula (I) with clopyralid (162); a compound of formula (I) with 2,4-D (211); a compound of formula (I) with dicamba (228); a compound of formula (I) with diphenamid (274); a compound of formula (I) with MCPA (499); a compound of formula (I) with quinclorac (712); a compound of formula (I) with aminopyralid (CAS RN 150114-71-9); a compound of formula (I) with 4-amino-3-chloro-6-(4-chloro-2-fluoro-3-methoxyphenyl)-2-pyridinecarboxylic acid (CAS RN 943832-60-8); or a compound of formula (I) with 4-amino-3-chloro-6-(4-chloro-2-fluoro-3-methoxyphenyl)-2-pyridinecarboxylic acid, methyl ester (CAS RN 943831-98-9)).

Mixtures of a compound of formula (I) with diflufenzopyr (252).

Mixtures of a compound of formula (I) with an acetanilide (e.g. a compound of formula (I) with acetochlor (5), a compound of formula (I) with dimethenamid (260), a compound of formula (I) with metolachlor (548), a compound of formula (I) with S-metolachlor (549), or a compound of formula (I) with pretilachlor (656)).

Mixtures of a compound of formula (I) with flamprop-M (355).

Mixtures of a compound of formula (I) with flufenacet (BAY FOE 5043) (369).

Mixtures of a compound of formula (I) with pyroxasulfone (CAS RN 447399-55-5).

Mixtures of a compound of formula (I) with an HPPD inhibitor (e.g. a compound of formula (I) with isoxaflutole (479), a compound of formula (I) with mesotrione (515), a compound of formula (I) with pyrasulfotole (CAS RN 365400-11-9), a compound of formula (I) with sulcotrione (747), a compound of formula (I) with tembotrione (CAS RN 335104-84-2), compound of formula (I) with topramezone (CAS RN 210631-68-8), a compound of formula (I) with 4-hydroxy-3-[[2-[(2-methoxyethoxy)methyl]-6-(trifluoromethyl)-3-pyridinyl]carbonyl]bicyclo[3.2.1]oct-3-en-2-one (CAS RN 352010-68-a 5), or compound of formula (I) with 4-hydroxy-3-[[2-(3-methoxypropyl)-6-(difluoromethyl)-3-pyridinyl]-carbonyl]bicyclo[3.2.1]oct-3-en-2-one (CAS RN 894355-80-7)).

Mixtures, of a compound of formula (I) with a triazine (e.g. a compound of formula (I) with atrazine (37); or a compound of formula (I) with terbuthylazine (775)).

Mixtures of a compound of formula (I) with a triazine and an HPPD inhibitor (e.g. a compound of formula (I) with triazine with isoxaflutole, a compound of formula (I) with triazine with mesotrione, a compound of formula (I) with triazine with pyrasulfotole, a compound of formula (I) with triazine with sulcotrione, a compound of formula (I) with triazine with tembotrione, a compound of formula (I) with triazine with topramezone, compound of formula (I) with triazine with 4-hydroxy-3-[[2-[(2-methoxyethoxy)methyl]-6-(trifluoromethyl)-3-pyridinyl]carbonyl]-bicyclo[3.2.1]oct-3-en-2-one, or a compound of formula (I) with triazine with 4-hydroxy-3-[[2-(3-methoxypropyl)-6-(difluoromethyl)-3-pyridinyl]carbonyl]-bicyclo[3.2.1]oct-3-en-2-one).

Mixtures of a compound of formula (I) with glyphosate (419).

Mixtures of a compound of formula (I) with glyphosate and an HPPD inhibitor (e.g. a compound of formula (I) with glyphosate with isoxaflutole, a compound of formula (I) with glyphosate with mesotrione, a compound of formula (I) with glyphosate with pyrasulfotole, a compound of formula (I) with glyphosate with sulcotrione, a compound of formula (I) with glyphosate with tembotrione, a compound of formula (I) with glyphosate with topramezone, a compound of formula (I) with glyphosate with 4-hydroxy-3-[[2-[(2-methoxyethoxy)methyl]-6-(trifluoromethyl)-3-pyridinyl]carbonyl]-bicyclo[3.2.1]oct-3-en-2-one, or a compound of formula (I) with glyphosate with 4-hydroxy-3-[[2-(3-methoxypropyl)-6-(difluoromethyl)-3-pyridinyl]carbonyl]-bicyclo[3.2.1]oct-3-en-2-one).

Mixtures of a compound of formula (I) with glufosinate-ammonium (418).

Mixtures of a compound of formula (I) with glufosinate-ammonium and an HPPD inhibitor (e.g. a compound of formula (I) with glufosinate-ammonium with isoxaflutole, a compound of formula (I) with glufosinate-ammonium with mesotrione, a compound of formula (I) with glufosinate-ammonium with pyrasulfotole, a compound of formula (I) with glufosinate-ammonium with sulcotrione, a compound of formula (I) with glufosinate-ammonium with tembotrione, a compound of formula (I) with glufosinate-ammonium with topramezone, a compound of formula (I) with glufosinate-ammonium with 4-hydroxy-3-[[2-[(2-methoxyethoxy)methyl]-6-(trifluoromethyl)-3-pyridinyl]carbonyl]-bicyclo[3.2.1]oct-3-en-2-one, or a compound of formula (I) with glufosinate-ammonium with 4-hydroxy-3-[[2-(3-methoxypropyl)-6-(difluoromethyl)-3-pyridinyl]carbonyl]-bicyclo[3.2.1]oct-3-en-2-one).

Mixtures of a compound of formula (I) with an ALS or an AHAS inhibitor (e.g. a compound of formula (I) with bensulfuron-methyl (64), a compound of formula (I) with chlorimuron-ethyl (135), compound of formula (I) with cloransulam-methyl (164), a compound of formula (I) with florasulam (359), a compound of formula (I) with flucarbazone-sodium (364), a compound of formula (I) with imazamox (451), a compound of formula (I) with imazapyr (453), a compound of formula (I) with imazethapyr (455), a compound of formula (I) with iodosulfuron-methyl-sodium (466), a compound of formula (I) with mesosulfuron-methyl (514), a compound of formula (I) with nicosulfuron (577), a compound of formula (I) with penoxsulam (622), a compound of formula (I) with pyroxsulam (triflosulam) (CAS RN 422556-08-9), a compound of formula (I) with thifensulfuron-methyl (thiametu-ron-methyl) (795), a compound of formula (I) with triasulfuron (817), a compound of formula (I) with tribenuron-methyl (822), a compound of formula (I) with trifloxysulfuron-sodium (833), a compound of formula (I) with thiencarbazone (4-[(4,5-dihydro-3-methoxy-4-methyl-5-oxo-1H-1,2,4-triazol-1-yl)carbonylsulfamoyl]-5-methylthiophene-3-carboxylic acid, BAY636)), or a compound of formula (I) with thiencarbazone-methyl (methyl 4-[(4,5-dihydro-3-methoxy-4-methyl-5-oxo-1H-1,2,4-triazol-1-yl)carbonylsulfamoyl]-5-methylthiophene-3-carboxylate, CAS RN 317815-83-1, BAY636-methyl)).

Mixtures of a compound of formula (I) with a PPO inhibitor (e.g. compound of formula (I) with acifluorfen-sodium (7), a compound of formula (I) with butafenacil (101), a compound of formula (I) with carfentrazone-ethyl (121), a compound of formula (I) with cinidon-ethyl (152), a compound of formula (I) with flumioxazin (376), a compound of formula (I) with fomesafen (401), a compound of formula (I) with lactofen (486), or a compound of formula (I) with [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester) (CAS RN 353292-31-6)).

Mixtures of a compound of formula (I) with an ACCase inhibitor (e.g. a compound of formula (I) with butroxydim (106), a compound of formula (I) with clethodim (155), a compound of formula (I) with clodinafop-propargyl (156), a compound of formula (I) with cycloxydim (190), a compound of formula (I) with cyhalofop-butyl (195), a compound of formula (I) with diclofop-methyl (238), a compound of formula (I) with fenoxaprop-P-ethyl (339), a compound of formula (I) with fluazifop-butyl (361), a compound of formula (I) with fluazifop-P-butyl (362), a compound of formula (I) with haloxyfop (427), a compound of formula (I) with haloxyfop-P (428), a compound of formula (I) with propaquizafop (670), a compound of formula (I) with quizalofop (717), a compound of formula (I) with quizalofop-P (718), compound of formula (I) with sethoxydim (726), a compound of formula (I) with tepraloxydim (771), a compound of formula (I) with tralkoxydim (811)), or a compound of formula (I) with pinoxaden (CAS RN 243973-20-8).

Mixtures of a compound of formula (I) with prosulfocarb (683), or a compound of formula (I) with tri-allate (816).

Mixtures of a compound of formula (I) with bromoxynil (95), a compound of formula (I) with chloridazon (134), a compound of formula (I) with chlorotoluron (143), a compound of formula (I) with diuron (281), or a compound of formula (I) with metribuzin (554).

Mixtures of a compound of formula (I) with clomazone (159), a compound of formula (I) with diflufenican (251), a compound of formula (I) with flurochloridone (389), or a compound of formula (I) with flurtamone (392).

Mixtures of a compound of formula (I) with pendimethalin (621) or a compound of formula (I) with trifluralin (836).

Mixtures of a compound of formula (I) with difenzoquat metilsulfate (248).

Mixtures of a compound of formula (I) with diquat dibromide (276).

Mixtures of a compound of formula (I) with paraquat dichloride (614).

The mixing partners of the compound of formula (I) may also be in the form of esters or salts, as mentioned for example in The Pesticide Manual, 13th Edition (BCPC), 2003. The reference to glufosinate-ammonium also applies to glufosinate, the reference to cloransulam-methyl also applies to cloransulam, the reference to dimethenamid also applies to dimethenamid-P, the reference to flamprop-M also applies to flamprop, and the reference to pyrithiobac-sodium also applies to pyrithiobac, etc.

The mixing ratio of the compound of formula (I) to the mixing partner is preferably from 1:100 to 1000:1; more preferably from 1:100 to 1000:1 by weight.

The mixtures can advantageously be used in the above-mentioned formulations (in which case "active ingredient" relates to the respective mixture of compound of formula (I) with the mixing partner).

Additionally, one or more of the following herbicides or plant growth regulators can be used in combination with a compound of formula (I) according to the invention or in combination with a mixture as described above: aclonifen (8), acrolein (10), alachlor (14), alloxydim (18), ametryn (20), amicarbazone (21), amidosulfuron (22), aminocyclopyrachlor (CAS RN 858956-08-8), amitrole (aminotriazole) (25), ammonium sulfamate (26), anilofos (31), asulam (36), aviglycine (39), azafenidin (CAS RN 68049-83-2), azimsulfuron (43), BAS 800H (CAS RN 372137-35-4), beflubutamid (55), benazolin (57), bencarbazone (CAS RN 173980-17-1), benfluralin (59), benfuresate (61), bensulide (65), bentazone (67), benzfendizone (CAS RN 158755-95-4), benzobicyclon (69), benzofenap (70), bilanafos (bialaphos) (77), bispyribac-sodium (82), borax (86), bromacil (90), bromobutide (93), bromofenoxim (CAS RN 13181-17-4), butachlor (100), butamifos (102), butralin (105), butylate (108), cafenstrole (110), carbetamide (117), chlorbromuron (CAS RN 13360-45-7), chlorflurenol-methyl (133), chloroacetic acid (138), chlorpropham (144), chlorsulfuron (147), chlorthal-dimethyl (148), cinmethylin (153), cinosulfuron (154), clomeprop (160), cumyluron (180), cyanamide (182), cyanazine (183), cyclanilide (186), cycloate (187), cyclosulfamuron (189), daimuron (213), dalapon (214), dazomet (216), desmedipham (225), desmetryn (CAS RN 1014-69-3), dichlobenil (229), dichlorprop (234), dichlorprop-P (235), diclosulam (241), dimefuron (256), dimepiperate (257), dimethachlor (258), dimethametryn (259), dimethipin (261), dimethylarsinic acid (264), dinitramine (268), dinoterb (272), dipropetryn (CAS RN 4147-51-7), dithiopyr (280), DNOC (282), DSMA (CAS RN 144-21-8), endothal (295), EPTC (299), esprocarb (303), ethalfluralin (305), ethametsulfuron-methyl (306), ethephon (307), ethofumesate (311), ethoxyfen (CAS RN 188634-90-4), ethoxyfen-ethyl (CAS RN 131086-42-5), ethoxysulfuron (314), etobenzanid (318), fentrazamide (348), ferrous sulfate (353), flazasulfuron (356), fluazolate (isopropazol) (CAS RN 174514-07-9), flucetosulfuron (CAS RN 412928-75-7), fluchloralin (365), flufenpyr-ethyl (371), flumetralin (373), flumetsulam (374), flumiclorac-pentyl (375), flumipropyn (flumipropin) (CAS RN 84478-52-4), fluometuron (378), fluoroglycofen-ethyl (380), flupoxam (CAS RN 119126-15-7), flupropacil (CAS RN 120890-70-2), flupropanate (383), flupyrsulfuron-methyl-sodium (384), flurenol (387), fluridone (388), fluroxypyr (390), fluthiacet-methyl (395), foramsulfuron (402), fosamine (406), halosulfuron-methyl (426), HC-252 (429), hexazinone (440), imazamethabenz-methyl (450), imazapic (452), imazaquin (454), imazosulfuron (456), indanofan (462), ioxynil (467), isoproturon (475), isouron (476), isoxaben (477), isoxachlortole (CAS RN 141112-06-3), isoxapyrifop (CAS RN 87757-18-4), karbutilate (482), lenacil (487), linuron (489), MCPA-thioethyl (500), MCPB (501), mecoprop (503), mecoprop-P (504), mefenacet (505), mefluidide (507), metam (519), metamifop (mefluoxafop) (520), metamitron (521), metazachlor (524), methabenzthiazuron (526), methazole (CAS RN 20354-26-1), methylarsonic acid (536), 1-methylcyclopropene (538), methyldymron (539), methyl isothiocyanate (543), metobenzuron (547), metobromuron (CAS RN 3060-89-7), metosulam (552), metoxuron (553), metsulfuron-methyl (555), MK-616 (559), molinate (560), monolinuron (562), MSMA (CAS RN 2163-80-6), naproanilide (571), napropamide (572), naptalam (573), neburon (574), nipyraclofen (CAS RN 99662-11-0), n-methyl-glyphosate, nonanoic acid (583), norflurazon (584), oleic acid (fatty acids) (593), orbencarb (595), orthosulfamuron (CAS RN 213464-77-8), oryzalin (597), oxadiargyl (599), oxadiazon (600), oxasulfuron (603), oxaziclomefone (604), oxyfluorfen (610), pebulate (617), pentachlorophenol (623), pentanochlor (624), pentoxazone (625), pethoxamid (627), petrolium oils (628), phenmedipham (629), picloram (645), picolinafen (646), piperophos (650), primisulfuron-methyl (657), prodiamine (661), profluazol (CAS RN 190314-43-3), profoxydim (663), prohexadione calcium (664), prometon (665), prometryn (666), propachlor (667), propanil (669), propazine (672), propham (674), propisochlor (667), propoxycarbazone-sodium (procarbazone-sodium) (679), propyzamide (681), prosulfuron (684), pyraclonil (pyrazogyl) (CAS RN 158353-15-2), pyraflufen-ethyl (691), pyrazolynate (692), pyrazosulfuron-ethyl (694), pyrazoxyfen (695), pyribenzoxim (697), pyributicarb (698), pyridafol (CAS RN 40020-01-7), pyridate (702), pyriftalid (704), pyriminobac-methyl (707), pyrimisulfan (CAS RN 221205-90-9), pyrithiobac-sodium (709), quinmerac (713), quinoclamine (714), rimsulfuron (721), sequestrene, siduron (727), simazine (730), simetryn (732), sodium chlorate (734), sulfentrazone (749), sulfometuron-methyl (751), sulfosate (CAS RN 81591-81-3), sulfosulfuron (752), sulfuric acid (755), tar oils (758), TCA-sodium (760), tebutam (CAS RN 35256-85-0), tebuthiuron (765), tefuryltrione (CAS RN 473278-76-1), terbacil (772), terbumeton (774), terbutryn (776), thenylchlor (789), thidiazimin (CAS RN 123249-43-4), thiazafluron (CAS RN 25366-23-8), thiazopyr (793), thiobencarb (797), tiocarbazil (807), triaziflam (819), triclopyr (827), trietazine (831), triflusulfuron-methyl (837), trihydroxytriazine (CAS RN 108-80-5), trinexapac-ethyl (CAS RN 95266-40-3), tritosulfuron (843), N-[(1R,2S)-2,6-dimethyl-2,3-dihydro-1H-inden-1-yl]-6-(1-fluoroethyl)-1,3,5-triazine-2,4-diamine (CAS RN 950782-86-2), 1-(2-chloro-6-propylimidazo[1,2-b]pyridazin-3-ylsulfonyl)-3-(4,6-dimethoxypyrimidin-2-yl)urea (CAS RN 570415-88-2), and 5-(2,6-difluoro-benzyloxymethyl)-5-methyl-3-(3-methyl-thiophen-2-yl)-4,5-dihydro-isoxazole (CAS RN 403640-27-7).

The mixing partners of the compound of formula (I) may also be in the form of esters or salts, as mentioned e.g. in The Pesticide Manual, 13th Edition (BCPC), 2003. The reference to acifluorfen-sodium also applies to acifluorfen, and the reference to bensulfuron-methyl also applies to bensulfuron, etc.

The mixing ratio of the compound of formula (I) to the mixing partner is preferably from 1:100 to 1000:1; more preferably from 1:100 to 1000:1 by weight.

The mixtures can advantageously be used in the above-mentioned formulations (in which case "active ingredient" relates to the respective mixture of compound of formula (I) with the mixing partner).

The compounds of formula (I) according to the invention can also be used in combination with one or more safeners. Likewise, mixtures of a compound of formula (I) according to the invention with one or more further herbicides can also be used in combination with one or more safeners. The term "safener" as used herein means a chemical that when used in combination with a herbicide reduces the undesirable effects of the herbicide on non-target organisms, for example, a safener protects crops from injury by herbicides but does not prevent the herbicide from killing the weeds. The safeners can be AD-67 (11), benoxacor (63), cloquintocet-mexyl (163), cyometrinil (CAS RN 78370-21-5), cyprosulfamide (CAS RN 221667-31-8), dichlormid (231), dicyclonon (CAS RN 79260-71-2), fenchlorazole-ethyl (331), fenclorim (332), flurazole (386), fluxofenim (399), furilazole (413) and the corresponding R isomer, isoxadifen-ethyl (478), mefenpyr-diethyl (506), 2-methoxy-N-[[4-[[(methylamino)carbonyl]amino]phenyl]sulfonyl]-benzamide (CAS RN 129531-12-0), naphthalic anhydride (CAS RN 81-84-5), N-(2-methoxybenzoyl)-4-[methylaminocarbonyl)amino]benzenesulfonamide, and oxabetrinil (598). Particularly preferred are mixtures of a compound of formula (I) with benoxacor and a compound of formula (I) with cloquintocet-mexyl.

The safeners of the compound of formula (I) may also be in the form of esters or salts, as mentioned e.g. in The Pesticide Manual, 13th Edition (BCPC), 2003. The reference to cloquintocet-mexyl also applies to cloquintocet, and the reference to fenchlorazole-ethyl also applies to fenchlorazole, etc.

Preferably the mixing ratio of compound of formula (I) to safener is from 100:1 to 1:10, especially from 20:1 to 1:1; (preferably from 100:1 to 1:10, especially from 20:1 to 1:1, by weight).

The mixtures can advantageously be used in the above-mentioned formulations (in which case "active ingredient" relates to the respective mixture of compound of formula (I) with the safener). It is possible that the safener and a compound of formula (I) and one or more additional herbicide(s), if any, are applied simultaneously. For example, the safener, a compound of formula (I) and one or more additional herbicide(s), if any, might be applied to the locus pre-emergence or might be applied to the crop post-emergence. It is also possible that the safener and a compound of formula (I) and one or more additional herbicide(s), if any, are applied sequentially. For example, the safener might be applied before sowing the seeds as a seed treatment and a compound of formula (I) and one or more additional herbicides, if any, might be applied to the locus pre-emergence or might be applied to the crop post-emergence.

Preferred mixtures of a compound of formula (I) with further herbicides and safeners include:

Mixtures of a compound of formula (I) with S-metolachlor and a safener, particularly benoxacor.

Mixtures of a compound of formula (I) with isoxaflutole and a safener.

Mixtures of a compound of formula (I) with mesotrione and a safener.

Mixtures of a compound of formula (I) with sulcotrione and a safener.

Mixtures of a compound of formula (I) with a triazine and a safener.

Mixtures of a compound of formula (I) with a triazine and isoxaflutole and a safener.

Mixtures of a compound of formula (I) with a triazine and mesotrione and a safener.

Mixtures of a compound of formula (I) with a triazine and sulcotrione and a safener.

Mixtures of a compound of formula (I) with glyphosate and a safener.

Mixtures of a compound of formula (I) with glyphosate and isoxaflutole and a safener.

Mixtures of a compound of formula (I) with glyphosate and mesotrione and a safener.

Mixtures of a compound of formula (I) with glyphosate and sulcotrione and a safener.

Mixtures of a compound of formula (I) with glufosinate-ammonium and a safener.

Mixtures of a compound of formula (I) with glufosinate-ammonium and isoxaflutole and a safener.

Mixtures of a compound of formula (I) with glufosinate-ammonium and mesotrione and a safener.

Mixtures of a compound of formula (I) with glufosinate-ammonium and sulcotrione and a safener.

Mixtures of a compound of formula (I) with florasulam and a safener, particularly cloquintocet-mexyl.

Mixtures of a compound of formula (I) with clodinafop-propargyl and a safener, particularly cloquintocet-mexyl.

Mixtures of a compound of formula (I) with pinoxaden and a safener, particularly cloquintocet-mexyl.

Mixtures of a compound of formula (I) with bromoxynil and a safener, particularly cloquintocet-mexyl.

The following Examples further illustrate, but do not limit, the invention.

PREPARATION EXAMPLES

The following abbreviations were used in this section: s=singlet; bs=broad singlet; d=doublet; dd=double doublet; dt=double triplet; t=triplet, tt=triple triplet, q=quartet, sept=septet; m=multiplet; Me=methyl; Et=ethyl; Pr=propyl; Bu=butyl; M.p.=melting point; RT=retention time, MH$^+$=molecular mass of the molecular cation.

The following LC-MS methods were used to characterize the compounds:

Method A

Compounds characterised by HPLC-MS were analysed using a Waters 2777 injector, 2996 photodiode array, 2420 ELSD and Micromass ZQ2000 equipped with a Waters Atlantis dC18 column (column length 20 mm, internal diameter of column 3 mm, particle size 3 micron). The analysis was conducted using a three minute run time, according to the following gradient table:

| Time (mins) | Solvent A (%) | Solvent B (%) | Flow (ml/minute) |
| --- | --- | --- | --- |
| 0.00 | 95.0 | 5.0 | 1.300 |
| 2.50 | 0.0 | 100 | 1.300 |
| 2.80 | 0.0 | 100 | 1.300 |
| 2.90 | 95.0 | 5.0 | 1.300 |

Solvent A: H$_2$O with 0.05% trifluroacetic acid v/v. Solvent B: CH$_3$CN with 0.05% trifluroacetic acid v/v. The characteristic values obtained for each compound were the retention time (RT, recorded in minutes) and the molecular ion, typically the cation M+H$^+$.

Method B

Compounds characterised by HPLC-MS were analysed using a Waters 2777 injector, 2996 photodiode array, 2420 ELSD and Micromass ZQ2000 equipped with a Waters Atlantis T3 dC18 column (column length 50 mm, internal diameter of column 4.6 mm, particle size 3 micron). The analysis was conducted using a six minute run time, according to the following gradient table:

| Time (mins) | Solvent A (%) | Solvent B (%) | Flow (ml/minute) |
| --- | --- | --- | --- |
| 0.00 | 95.0 | 5.0 | 1.300 |
| 5.50 | 0.0 | 100 | 1.300 |
| 5.80 | 0.00 | 100 | 1.300 |
| 5.90 | 95.0 | 5.0 | 1.300 |

Solvent A: H$_2$O with 0.05% trifluroacetic acid. Solvent B: CH$_3$CN with 0.05% trifluroacetic acid. The characteristic values obtained for each compound were the retention time (RT, recorded in minutes) and the molecular ion, typically the cation M+H$^+$ 1. Reactions which are Covered by Scheme 1

Example 1.1

Preparation of 3-methyl-pyrazine-2-carboxylic acid ethyl ester

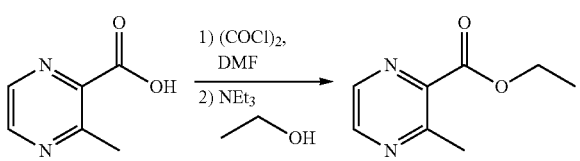

To a solution of 3-methyl-pyrazine-2-carboxylic acid (10 g) (commercially available) and N,N-dimethylformamide ("DMF") (1 drop) in dichloromethane (20 ml) at ambient temperature was added drop wise oxalyl chloride (2.57 ml). The reaction mixture was stirred at ambient temperature for 1 hour. The reaction mixture was concentrated and the residue dissolved in dichloromethane (20 ml). Triethylamine (4.04 ml) was added to this solution followed by drop wise addition of ethanol (10 ml). The reaction mixture was stirred at ambient temperature for one hour and then concentrated. The residue was purified by chromatography on silica gel (eluent: 0-10% v/v ethyl acetate in iso-hexane) to give 3-methyl-pyrazine-2-carboxylic acid ethyl ester (9.85 g). MH$^+$=167, RT=0.73 min (Method A). 1H-NMR (400 MHz, CDCl$_3$): 8.61 (d, 1H), 8.54 (d, 1H), 4.49 (q, 2H), 2.85 (s, 3H), 1.46 (t, 3H) ppm.

Example 1.2

Preparation of 3-methyl-pyrazine-2-carboxylic acid methyl ester

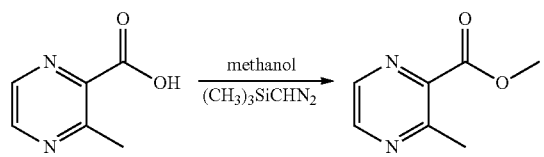

To a solution of 3-methyl-pyrazine-2-carboxylic acid (4.7 g) in toluene (70 ml) and methanol (30 ml) at ambient temperature was added drop wise (trimethylsilyl)diazomethane (2M in diethyl ether) (26 ml). The reaction mixture was stirred at ambient temperature for 1 hour. The reaction mixture was concentrated and purified by passing through a pad of silica and eluting with 30% v/v ethyl acetate in iso-hexane to give 3-methyl-pyrazine-2-carboxylic acid methyl ester (3.10 g). 1H-NMR (400 MHz, CDCl$_3$): 8.63 (d, 1H), 8.53 (d, 1H), 4.02 (s, 3H), 2.87 (s, 3H) ppm.

Example 1.3

Preparation of 3-bromomethyl-pyrazine-2-carboxylic acid ethyl ester

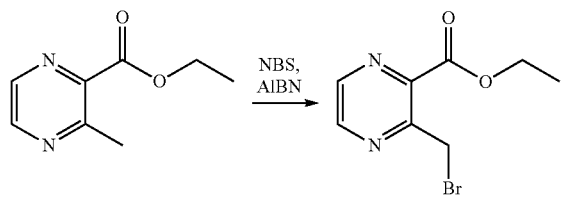

A mixture of 3-methyl-pyrazine-2-carboxylic acid ethyl ester (Example 1.1) (0.5 g), N-bromosuccinimide ("NBS") (0.536 g) and 2,2'-azobis(2-methylpropionitrile) ("AIBN") (0.487 g) in carbon tetrachloride (2.5 ml) was heated to reflux. After 1 hour thin layer chromatography showed a mixture of starting material and the desired product. Further NBS (0.536 g) and AIBN (0.243 g) were added and the reaction mixture heated for a further 1 hour. The percentage of product increased and impurities began to form. The reaction mixture was cooled to ambient temperature and then to 0° C. The cold mixture was filtered and the filtrate concentrated. The residue was purified by chromatography on silica gel (eluent: 0-10% v/v ethyl acetate in iso-hexane) to give 3-bromomethyl-pyrazine-2-carboxylic acid ethyl ester (640 mg) contaminated with 3-methyl-pyrazine-2-carboxylic acid ethyl ester (due to co-elution, ~3:2). MH$^+$=245, RT=1.26 min (Method A).

The following compound was made using the same method:

3-Bromomethyl-pyrazine-2-carboxylic acid methyl ester. 1H-NMR (400 MHz, CDCl$_3$): 8.71 (d, 1H), 8.64 (d, 1H), 5.03 (s, 2H), 4.06 (s, 3H) ppm.

2. Reactions Which are Covered by Scheme 2

Example 2.1

Preparation of 3-carbamimidoylsulfanylmethyl-pyrazine-2-carboxylic acid ethyl ester hydrobromide

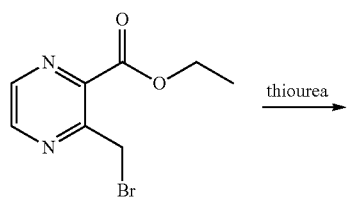

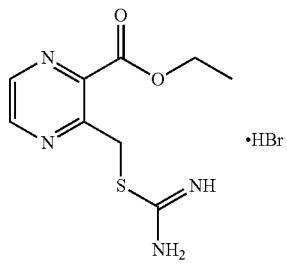

A suspension of thiourea (620 mg) and 3-bromomethyl-pyrazine-2-carboxylic acid ethyl ester (2 g) in tetrahydrofuran was heated in the microwave at 120° C. for 5 minutes. The product formed an oil so the tetrahydrofuran was simply decanted to leave 3-carbamimidoylsulfanylmethyl-pyrazine-2-carboxylic acid ethyl ester hydrobromide (2.2 g) as an oil. MH$^+$=241, RT=0.26 min (Method A).

Example 2.2

Preparation of 3-(2-chloro-5-trifluoromethyl-benzyl-sulfanylmethyl)-pyrazine-2-carboxylic acid ethyl ester (Compound No. A2 of Table A)

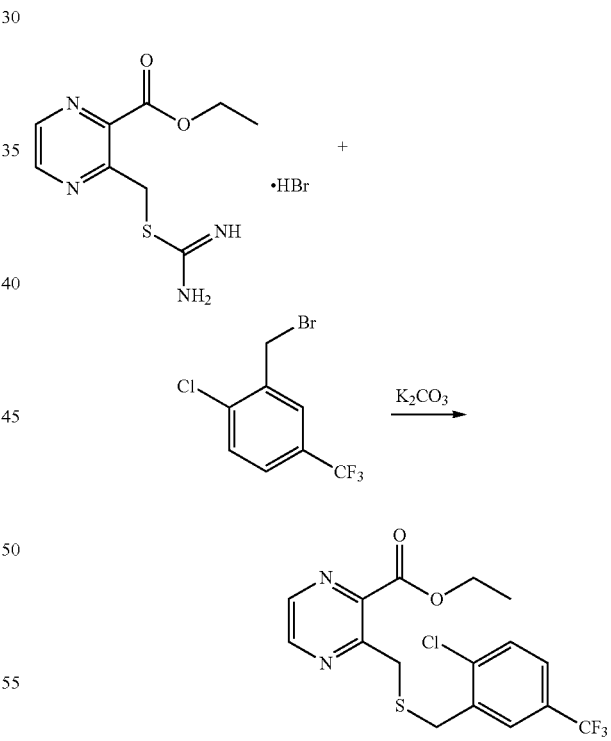

To a solution of 3-carbamimidoylsulfanylmethyl-pyrazine-2-carboxylic acid ethyl ester hydrobromide (0.367 g) in acetonitrile (2 ml) was added 2-chloro-5-trifluoromethyl-benzylbromide (commercially available) (0.294 g), potassium carbonate (0.316 g) and water (3 drops). The reaction mixture was heated to 120° C. for 10 minutes in the microwave. The reaction mixture was filtered and the filtrate concentrated. The residue was purified by chromatography on silica gel (eluent: 0-10% v/v ethyl acetate in iso-hexane) to give Compound No. A2 of Table A.

Example 2.3

Preparation of 2-(2,3-dichloro-6-fluoro-benzyl)-isothiourea hydrobromide (Compound No. 1 of Table 4)

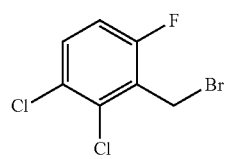

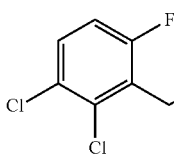

A mixture of thiourea (1.52 g) and 2,3-dichloro-6-fluorobenzyl bromide (commercially available) (5.16 g) in 2-butanone (20 ml) was heated to 100° C. for 5 minutes in the microwave. The reaction mixture was cooled to ambient temperature and filtered. The white solid was washed with diethyl ether to give 2-(2,3-dichloro-6-fluoro-benzyl)-isothiourea hydrobromide (5.14 g). 1H-NMR (400 MHz, CD$_3$OD): 7.61-7.65 (m, 1H), 7.22-7.27 (m, 1H), 4.64 (m, 2H) ppm.

Table 9 discloses isothioureas of formula (8) where H-LG and R$^4$ has the values given in Table 9.

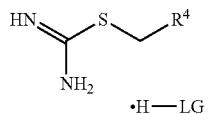

(8)

Example 2.4

Preparation of 3-(2,3-dichloro-6-fluoro-benzylsulfanylmethyl)-pyrazine-2-carboxylic acid methyl ester (Compound No. A1 of Table A)

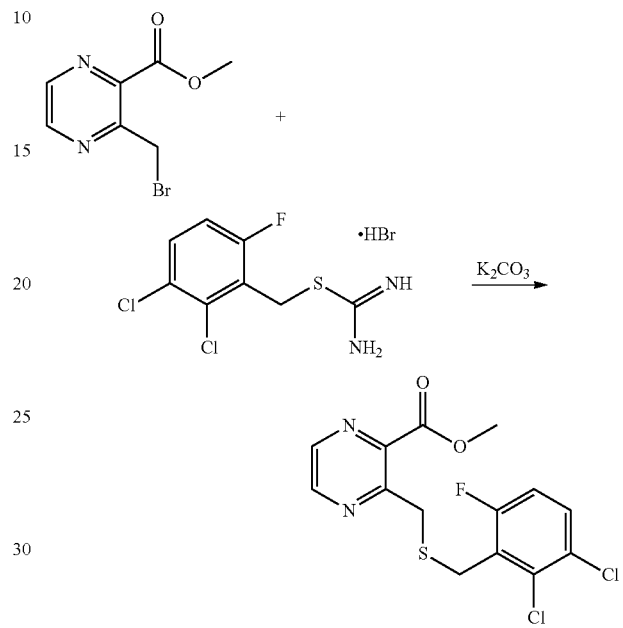

To a mixture of 3-bromomethyl-pyrazine-2-carboxylic acid methyl ester (2.5 g) and 2-(2,3-dichloro-6-fluoro-benzyl)-isothiourea hydrobromide (2.75 g) in acetonitrile (20 ml) was added potassium carbonate (3.8 g). The reaction mixture was stirred at ambient temperature for 5 hours, then stored at ambient temperature for 16 hours. The reaction mixture was poured into aqueous hydrochloric acid (2M) and extracted with ethyl acetate. The phases were separated and the organic

TABLE 9

| Comp. No. | R$^4$ | H—LG | MH$^+$ | RT (min) | LC-MS Method |
|---|---|---|---|---|---|
| 1 | 2,3-dichloro-6-fluoro-phenyl- | H—Br | — | — | — |
| 2 | 5-chloro-2-trifluoromethyl-phenyl- | H—Br | 269 | 1.07 | A |
| 3 | 2-chloro-6-trifluoromethyl-phenyl- | H—Br | 269 | 1.17 | A |
| 4 | 2-iodo-phenyl- | H—Br | 292 | 0.95 | A |
| 5 | 2-chloro-5-fluoro-phenyl- | H—Br | 219 | 0.40 | A |
| 6 | 2,5-bis-trifluoromethyl-phenyl- | H—Br | 303 | 1.08 | A |
| 7 | 4-chloro-2-trifluoromethyl-phenyl- | H—Br | 269 | 1.08 | A |
| 8 | 2,3,6-trichloro-phenyl- | H—Br | 271 | 1.08 | A |
| 9 | 2,6-dichloro-phenyl- | H—Br | 235 | 1.22 | A |
| 10 | 2,4,6-trimethyl-phenyl- | H—Cl | 209 | 1.13 | A |
| 11 | 3-bromo-2-chloro-6-fluoro-phenyl- | H—Br | 298 | 1.28 | A |
| 12 | 4-bromo-2-trifluoromethyl-phenyl- | H—Br | 312 | 1.07 | A |
| 13 | 2,4,6-trichloro-phenyl- | H—Cl | 269 | 1.01 | A |
| 14 | 2-bromo-5-chloro-phenyl- | H—Br | 281 | 1.11 | A |
| 15 | 2-chloro-6-fluoro-3-trifluoromethyl-phenyl- | H—Br | 287 | 1.25 | A |
| 16 | 2-bromo-phenyl- | H—Br | 247 | 1.05 | A |
| 17 | 2,6-dichloro-4-trifluoromethyl-phenyl- | H—Cl | 303 | 1.12 | A |
| 18 | 4-chloro-2-methanesulfonyl-phenyl- | H—Br | 279 | 1.14 | A |
| 19 | 2-chloro-5-trifluoromethyl-phenyl- | H—Br | 269 | 1.07 | A |
| 20 | 2-methyl-phenyl- | H—Br | 181 | 0.92 | A | layer was washed with saturated aqueous sodium hydrogen carbonate (saturated) and brine. The organic layer was concentrated and the residue purified by chromatography on silica gel (eluent: 0-10% v/v ethyl acetate in hexane) to give Compound No. A1 of Table A (0.26 g). 1H-NMR (400 MHz, CDCl$_3$): 8.63 (d, 1H), 8.59 (d, 1H), 7.30-7.34 (m, 1H), 6.91-6.95 (m, 1H), 4.37 (m, 2H), 4.00 (s, 3H), 3.99 (m, 2H) ppm.

Compound Nos. A1 to A29 of Table A were made using methods analogous to those described in Example 2.1, Example 2.2, Example 2.3 and Example 2.4.

Table A discloses 31 thioethers of formula (6a) where $R^4$ and $R^{10}$ have the values given in Table A. Compounds of formula (6a) are compounds of formula (6) where $R^1$ and $R^2$ are each hydrogen.

3. Reactions Which are Covered by Scheme 3

Example 3.1

Preparation of 3-(2,3-dichloro-6-fluoro-phenyl-methanesulfonylmethyl)-pyrazine-2-carboxylic acid methyl ester (Compound No. B1 of Table B)

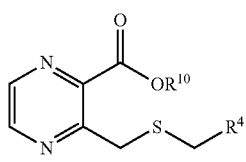

(6a)

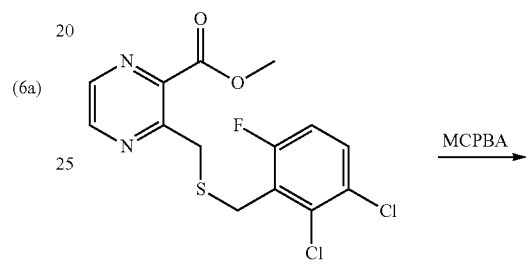

MCPBA

TABLE A

| Comp. No. | $R^4$ | $R^{10}$ | MH+ | RT (min) | LC-MS Method |
|---|---|---|---|---|---|
| A1 | 2,3-dichloro-6-fluoro-phenyl- | methyl- | — | — | — |
| A2 | 2-chloro-5-trifluoromethyl-phenyl- | ethyl- | 391 | 1.74 | A |
| A3 | 3-chloro-5-trifluoromethyl-phenyl- | ethyl- | 391 | 1.69 | A |
| A4 | 2-fluoro-6-methyl-phenyl- | ethyl- | 321 | 1.52 | A |
| A5 | 2-chloro-6-fluoro-5-methoxy-phenyl- | ethyl- | 371 | 1.48 | A |
| A6 | 2-fluoro-6-trifluoromethyl-phenyl- | ethyl- | 375 | 1.57 | A |
| A7 | 5-chloro-2-trifluoromethyl-phenyl- | ethyl- | 391 | 1.69 | A |
| A8 | 2-chloro-4-fluoro-phenyl- | ethyl- | 341 | 1.70 | A |
| A9 | 2-difluoromethoxy-phenyl- | ethyl- | 355 | 1.56 | A |
| A10 | 3-fluoro-2-trifluoromethyl-phenyl- | ethyl- | 375 | 1.71 | A |
| A11 | 2-trifluoromethyl-phenyl- | ethyl- | 357 | 1.69 | A |
| A12 | 2-chloro-3,6-difluoro-phenyl- | ethyl- | 359 | 1.59 | A |
| A13 | 2-chloro-6-trifluoromethyl-phenyl- | ethyl- | 391 | 1.77 | A |
| A14 | 2-iodo-phenyl- | ethyl- | 415 | 1.62 | A |
| A15 | 2-chloro-5-fluoro-phenyl- | ethyl- | 341 | 1.59 | A |
| A16 | 2,5-bis-trifluoromethyl-phenyl- | ethyl- | 425 | 1.77 | A |
| A17 | 4-chloro-2-trifluoromethyl-phenyl- | ethyl- | 391 | 1.76 | A |
| A18 | 2,3,6-trichloro-phenyl- | ethyl- | 393 | 1.75 | A |
| A19 | 2,6-dichloro-phenyl- | ethyl- | 357 | 1.63 | A |
| A20 | 2,4,6-trimethyl-phenyl- | ethyl- | 331 | 1.75 | A |
| A21 | 3-bromo-2-chloro-6-fluoro-phenyl- | ethyl- | 421 | 1.69 | A |
| A22 | 4-bromo-2-trifluoromethyl-phenyl- | ethyl- | 437 | 1.79 | A |
| A23 | 2,4,6-trichloro-phenyl- | ethyl- | 393 | 1.88 | A |
| A24 | 2-bromo-5-chloro-phenyl- | ethyl- | 401 | 1.62 | A |
| A25 | 2-chloro-6-fluoro-3-trifluoromethyl-phenyl- | ethyl- | 409 | 1.54 | A |
| A26 | 2-bromo-phenyl- | ethyl- | 367 | 1.45 | A |
| A27 | 2,6-dichloro-4-trifluoromethyl-phenyl- | ethyl- | 425 | 1.66 | A |
| A28 | 4-chloro-2-methanesulfonyl-phenyl- | ethyl- | 401 | 1.31 | A |
| A29 | 2-methyl-phenyl- | ethyl- | 303 | 1.51 | A |
| A30 | 2-chloro-6-fluoro-3-trifluoromethyl-phenyl- | ethyl- | 409 | 1.73 | A |
| A31 | 2,6-dichloro-3-trifluoromethyl-phenyl- | ethyl- | 425 | 1.82 | A |

-continued

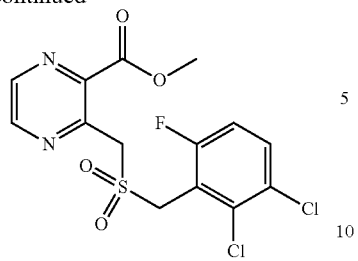

To a solution of 3-(2,3-dichloro-6-difluoro-benzylsulfanylmethyl)-pyrazine-2-carboxylic acid methyl ester (0.26 g) in dichloromethane (10 ml) was added 3-chloroperoxybenzoic acid ("MCPBA") (0.31 g). The reaction mixture was stirred at ambient temperature for 16 hours. The reaction was quenched by addition of aqueous sodium hydrogen carbonate (saturated) and aqueous sodium thiosulfate (saturated) and the mixture stirred for 2 hours. The phases were separated and the aqueous layer extracted with further dichloromethane (2×20 ml). The combined organic layers were concentrated to give Compound No. B1 of Table B (0.26 g).

The following compounds were made using an analogous method:

3-(2',4'-Dichloro-4-ethyl-biphenyl-3-ylmethanesulfonylmethyl)-pyrazine-2-carboxylic acid ethyl ester [Compound No. B29 of Table B] 1H-NMR (400 MHz, CDCl$_3$): 1.26 (3H, t), 1.45 (3H, t), 2.80-2.85 (2H, q), 4.47-4.53 (q, 2H), 5.17 (2H, s), 7.29 (2H, d), 7.38 (1H, s), 7.39 (1H, d), 7.47-7.48 (1H, m), 7.61 (1H, d), 8.74 (1H, d), 8.75 (1H, d).

Compound Nos. B1 to B31 of Table B were made using a method analogous to that described in Example 3.1.

Table B discloses 31 sulfones of formula (9a) where $R^4$ and $R^{10}$ have the values given in Table B. Compounds of formula (9a) are compounds of formula (9) where $R^1$ and $R^2$ are each hydrogen.

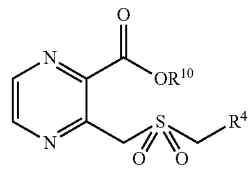

(9a)

TABLE B

| Comp. No. | $R^4$ | $R^{10}$ | MH+ | RT (min) | LC-MS Method |
|---|---|---|---|---|---|
| B1 | 2,3-dichloro-6-fluoro-phenyl- | methyl- | 393 | 1.44 | A |
| B2 | 2-chloro-5-trifluoromethyl-phenyl- | ethyl- | 423 | 1.57 | A |
| B3 | 3-chloro-5-trifluoromethyl-phenyl- | ethyl- | 423 | 1.47 | A |
| B4 | 2-fluoro-6-methyl-phenyl- | ethyl- | 353 | 1.28 | A |
| B5 | 2-chloro-6-fluoro-5-methoxy-phenyl- | ethyl- | 403 | 1.27 | A |
| B6 | 2-fluoro-6-trifluoromethyl-phenyl | ethyl- | 407 | 1.36 | A |
| B7 | 5-chloro-2-trifluoromethyl-phenyl- | ethyl- | 423 | 1.44 | A |
| B8 | 2-chloro-4-fluoro-phenyl- | ethyl- | 373 | 1.24 | A |
| B9 | 2-difluoromethoxy-phenyl- | ethyl- | 387 | 1.23 | A |
| B10 | 3-fluoro-2-trifluoromethyl-phenyl- | ethyl- | 407 | 1.35 | A |
| B11 | 2-trifluoromethyl-phenyl- | ethyl- | 389 | 1.26 | A |
| B12 | 2-chloro-3,6-difluoro-phenyl- | ethyl- | 391 | 1.22 | A |
| B13 | 2-chloro-6-trifluoromethyl-phenyl- | ethyl- | 423 | 1.43 | A |
| B14 | 2-iodo-phenyl- | ethyl- | 447 | 3.69 | B |
| B15 | 2-chloro-5-fluoro-phenyl- | ethyl- | 373 | 3.63 | B |
| B16 | 2,5-bis-trifluoromethyl-phenyl- | ethyl- | 457 | 1.61 | A |
| B17 | 4-chloro-2-trifluoromethyl-phenyl- | ethyl- | 423 | 1.53 | A |
| B18 | 2,3,6-trichloro-phenyl- | ethyl- | 424 | 1.50 | A |
| B19 | 2,6-dichloro-phenyl- | ethyl- | 389 | 1.38 | A |
| B20 | 2,4,6-trimethyl-phenyl- | ethyl- | 363 | 4.05 | B |
| B21 | 3-bromo-2-chloro-6-fluoro-phenyl- | ethyl- | 453 | 3.87 | B |
| B22 | 4-bromo-2-trifluoromethyl-phenyl- | ethyl- | 469 | 4.17 | B |
| B23 | 2,4,6-trichloro-phenyl- | ethyl- | 423 | 1.47 | A |
| B24 | 2-bromo-5-chloro-phenyl- | ethyl- | 433 | 1.27 | A |
| B25 | 2-chloro-6-fluoro-3-trifluoromethyl-phenyl- | ethyl- | 441 | 1.30 | A |
| B26 | 2-bromo-phenyl- | ethyl- | 399 | 1.16 | A |
| B27 | 2,6-dichloro-4-trifluoromethyl-phenyl- | ethyl- | 457 | 1.38 | A |
| B28 | 4-chloro-2-methanesulfonyl-phenyl- | ethyl- | 433 | 1.12 | A |
| B29 | 2-Et-4-(2',4'-diCl—Ph)-phenyl- | ethyl- | — | — | |
| B30 | 2-chloro-6-fluoro-3-trifluoromethyl-phenyl- | ethyl- | 441 | 1.52 | A |
| B31 | 2,6-dichloro-3-trifluoromethyl-phenyl- | ethyl- | 457 | 1.53 | A |

Example 3.2

Preparation of 7-(2,3-dichloro-6-fluoro-phenyl)-6,6-dioxo-5,6-dihydro-6-λ-6-thia-1,4-diaza-naphthalen-8-ol (Compound No. C1 of Table C)

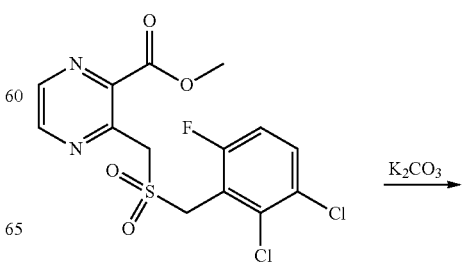

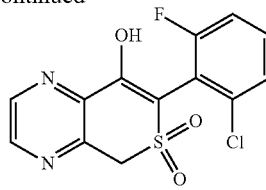

A mixture of 3-(2,3-dichloro-6-fluoro-phenylmethane-sulfonylmethyl)-pyrazine-2-carboxylic acid methyl ester (0.261 g) and potassium carbonate (0.182 g) in N,N-dimethylformamide (6 ml) was heated to 100° C. for 2 hours. The reaction mixture was cooled to ambient temperature, diluted with water and washed with diethyl ether. The aqueous layer was acidified with aqueous hydrochloric acid (2M) and the resulting precipitate isolated by filtration. The precipitate was washed with water and diethyl ether and dried to give Compound No. C1 of Table C (0.106 g). MH$^+$=361, RT=1.35 min.

Compound Nos. C1 to C27 of Table C were made using a method analogous to that described in Example 3.2.

Table C discloses 27 6,6-dioxo-6-thia-1,4-diaza-naphthalenes of formula (10a) where $R^4$ has the values given in Table C. Compounds of formula (10a) are compounds of formula (10) where $R^1$ and $R^2$ are each hydrogen.

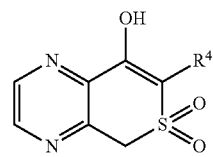

(10a)

TABLE C

| Comp. No. | $R^4$ | RT (min) | LC-MS MH$^+$ | Method | 1H-NMR (400 MHz, chemical shifts in ppm) |
|---|---|---|---|---|---|
| C1 | 2,3-dichloro-6-fluoro-phenyl- | 1.35 | 361 | A | |
| C2 | 2-chloro-5-trifluoromethyl-phenyl- | 1.41 | 377 | A | |
| C3 | 3-chloro-5-trifluoromethyl-phenyl- | 1.40 | 377 | A | |
| C4 | 2-fluoro-6-methyl-phenyl- | 1.21 | 307 | A | |
| C5 | 2-chloro-6-fluoro-5-methoxy-phenyl- | 1.21 | 357 | A | |
| C6 | 2-fluoro-6-trifluoromethyl-phenyl- | 1.29 | 361 | A | |
| C7 | 5-chloro-2-trifluoromethyl-phenyl- | 1.30 | 377 | A | |
| C8 | 2-chloro-4-fluoro-phenyl- | 1.20 | 327 | A | |
| C9 | 2-difluoromethoxy-phenyl- | 1.04 | 341 | A | |
| C10 | 3-fluoro-2-trifluoromethyl-phenyl- | 1.11 | 361 | A | |
| C11 | 2-trifluoromethyl-phenyl- | 1.05 | 343 | A | |
| C12 | 2-chloro-3,6-difluoro-phenyl- | 1.04 | 345 | A | |
| C13 | 2-chloro-6-trifluoromethyl-phenyl- | 1.20 | 377 | A | |
| C14 | 2-iodo-phenyl- | 1.18 | 401 | A | |
| C15 | 2-chloro-5-fluoro-phenyl- | 1.16 | 327 | A | |
| C16 | 2,5-bis-trifluoromethyl-phenyl- | 1.40 | 411 | A | |
| C17 | 4-chloro-2-trifluoromethyl-phenyl- | 1.35 | 377 | A | |
| C18 | 2,3,6-trichloro-phenyl- | 1.30 | 377 | A | |
| C19 | 2,6-dichloro-phenyl- | 1.14 | 343 | A | |
| C20 | 2,4,6-trimethyl-phenyl- | 1.33 | 317 | A | |
| C21 | 3-bromo-2-chloro-6-fluoro-phenyl- | 1.28 | 407 | A | |
| C22 | 4-bromo-2-trifluoromethyl-phenyl- | 1.35 | 423 | A | |
| C23 | 2,4,6-trichloro-phenyl- | — | — | — | 8.83 (d, 1H), 8.78 (d, 1H), 7.79 (s, 2H), 5.05 (s, 3H). d$_6$-DMSO |
| C24 | 2-Et-4-(2',4'-diCl—Ph)-phenyl- | — | — | — | 1.30 (3H, t), 2.80 (2H, q), 4.90 (2H, s), 7.30 (1H, d), 7.35 (1H, d), 7.45-7.55 (4H, m), 8.20 (1H, bs), 8.65 (1H, s), 8.70 (1H, s) CDCl$_3$ |
| C25 | 2-bromo-5-chloro-phenyl- | 1.29 | 387 | A | |
| C26 | 2-bromo-phenyl- | 1.12 | 353 | A | |
| C27 | 2-chloro-6-fluoro-3-trifluoromethyl-phenyl- | 1.38 | 395 | A | |

4. Reactions Which are Covered by Scheme 4

Example 4.1

Preparation of 7-(5-chloro-2-trifluoromethyl-phenyl)-8-ethoxymethoxy-5H-6-thia-1,4-diaza-naphthalene 6,6-dioxide (Compound No. X1)

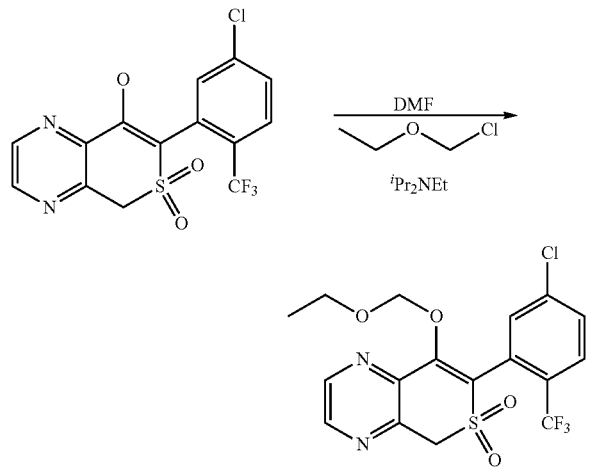

To a mixture of 7-(5-chloro-2-trifluoromethyl-phenyl)-6,6-dioxo-5,6-dihydro-6-thia-1,4-diaza-naphthalen-8-ol (Compound C7 of Table C) (0.54 g) and N,N-diisopropylethylamine (0.25 ml) in N,N-dimethylformamide (5 ml) under nitrogen atmosphere was added chloromethyl ethyl ether (0.20 ml) and the reaction mixture was stirred at ambient temperature. After 2 hr further diisopropylethylamine (0.10 ml) and chloromethyl ethyl ether (0.10 ml) were added. After a further 3 hours stirring the reaction was concentrated and the residue purified by chromatography on silica gel (eluent: 0-100% v/v ethyl acetate in hexane) to give 7-(5-chloro-2-trifluoromethyl-phenyl)-8-ethoxymethoxy-5H-6-thia-1,4-diaza-naphthalene 6,6-dioxide (0.276 g) 1H-NMR (400 MHz, CDCl$_3$): 1.04 (3H, t), 3.25-3.41 (2H, m), 4.76-4.87 (2H, q), 5.13 (1H, d), 5.33 (1H, d), 7.58-7.61 (2H, m), 7.76 (1H, d), 8.62 (1H, d), 8.73 (1H, d).

Example 4.2

Preparation of isobutyric acid 7-(3-bromo-2-chloro-6-fluoro-phenyl)-6,6-dioxo-5,6-dihydro-6-thia-1,4-diaza-naphthalen-8-yl ester (Compound No. X2)

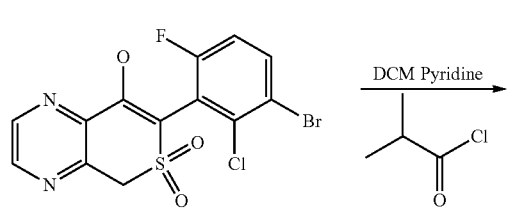

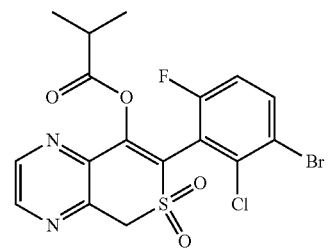

To a solution of 7-(3-bromo-2-chloro-6-fluoro-phenyl)-6,6-dioxo-5,6-dihydro-6-thia-1,4-diaza-naphthalen-8-ol (Compound C21 of Table C) (0.5 g) in dichloromethane (5 ml) at 0° C. was added pyridine (0.12 ml) followed by drop wise addition of isobutyryl chloride (0.142 ml). The reaction mixture was stirred at ambient temperature for 2 hours. The reaction mixture was concentrated and the residue purified by chromatography on silica gel (eluent: 0-100% v/v ethyl acetate in hexane) to give isobutyric acid 7-(3-bromo-2-chloro-6-fluoro-phenyl)-6,6-dioxo-5,6-dihydro-6-thia-1,4-diaza-naphthalen-8-yl ester (0.17 g) 1H-NMR (400 MHz, CDCl$_3$): 1.15 (6H, d), 2.80 (1H, quin), 5.00 (2H, s), 7.10 (1H, t), 7.70 (1H, m), 8.65 (1H, d), 8.70 (1H, d).

The following compounds were made using an analogous method:

Isobutyric acid 7-(2-bromo-5-chloro-phenyl)-6,6-dioxo-5,6-dihydro-6-thia-1,4-diaza-naphthalen-8-yl ester, MH$^+$=457, RT=1.69 min (Method A).

2,2-Dimethyl-propionic acid 7-(2-bromo-5-chloro-phenyl)-6,6-dioxo-5,6-dihydro-6-thia-1,4-diaza-naphthalen-8-yl ester, MH$^+$=471, RT=1.78 min (Method A).

Isobutyric acid 7-(2-bromo-phenyl)-6,6-dioxo-5,6-dihydro-6-thia-1,4-diaza-naphthalen-8-yl ester, MH$^+$=423, RT=1.58 min (Method A).

2,2-Dimethyl-propionic acid 7-(2-bromo-phenyl)-6,6-dioxo-5,6-dihydro-6-thia-1,4-diaza-naphthalen-8-yl ester, MH$^+$=437, RT=1.69 min (Method A).

Example 4.3

Preparation of 7-(5-chloro-2-trifluoromethyl-phenyl)-5,5-cyclopropyl-6,6-dioxo-5,6-dihydro-6-thia-1,4-diaza-naphthalen-8-ol (Compound No. F11 of Table F)

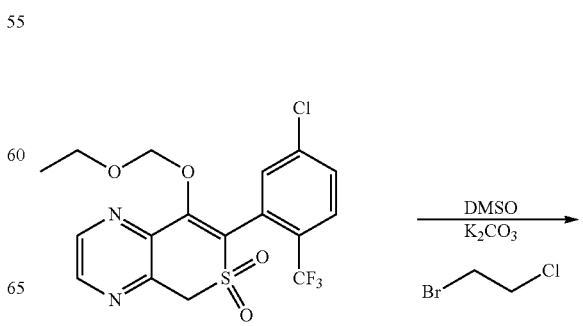

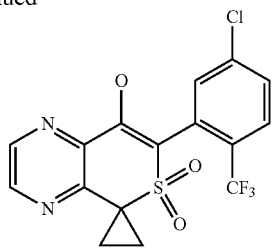

A mixture of 7-(5-chloro-2-trifluoromethyl-phenyl)-8-ethoxymethoxy-5H-6-thia-1,4-diaza-naphthalene 6,6-dioxide (0.045 g), 1-bromo-2-chloroethane (0.013 ml) and potassium carbonate (0.085 g) in dimethylsulfoxide (1 ml) was stirred at ambient temperature for 18 hours. The reaction mixture was diluted with water, quenched with 2M aqueous hydrochloric acid and extracted with diethyl ether. The organic layer was concentrated and the residue purified by reverse phase chromatography (eluent: 0-100% v/v acetonitrile in water with 0.05% trifluoroacetic acid) to give 7-(5-chloro-2-trifluoromethyl-phenyl)-5,5-cyclopropyl-6,6-dioxo-5,6-dihydro-6-thia-1,4-diaza-naphthalen-8-ol Compound No. F11 of Table F; (0.013 g). MH$^+$=403, RT=1.44 min.

The following compound was made using an analogous method:

Compound No. F5 of Table F.

Example 4.4

Preparation of isobutyric acid 7-(3-bromo-2-chloro-6-fluorophenyl)-5-ethyl-6,6-dioxo-5,6-dihydro-6-thia-1,4-diaza-naphthalen-8-yl ester

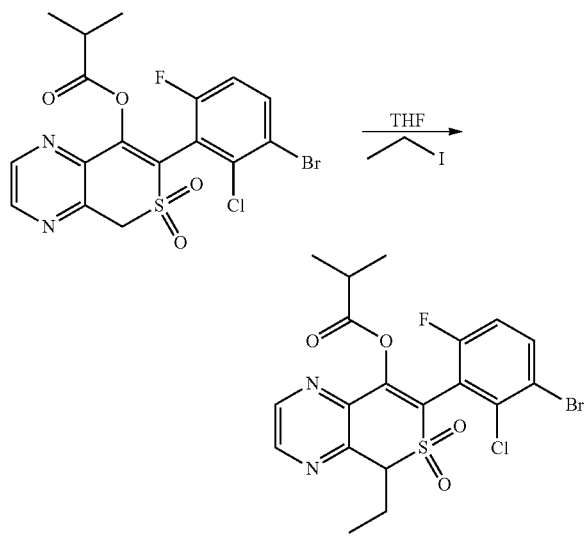

To a solution of Compound No. X2 (Example 4.2) (0.1 g) in tetrahydrofuran (1 ml) was added 1,8-diazabicyclo[5.4.0]undec-7-ene (0.038 ml) followed by ethyl iodide (0.017 ml). The reaction mixture was heated at 60° C. for 1 hour. The reaction mixture was concentrated and the residue purified by chromatography on silica gel (eluent: 0-100% v/v ethyl acetate in hexane) to give isobutyric acid 7-(3-bromo-2-chloro-6-fluorophenyl)-5-ethyl-6,6-dioxo-5,6-dihydro-6-thia-1,4-diaza-naphthalen-8-yl ester (0.011 g) 1H-NMR (400 MHz, CDCl$_3$): 1.05-1.20 (9H, m), 2.35 (1H, m), 2.55 (1H, m), 2.75 (1H, m), 4.40 (1H, m), 7.05 (1H, m), 7.75 (1H, m), 8.60 (1H, s), 8.65 (1H, s).

The following compounds were made using an analogous method:

Isobutyric acid 7-(3-bromo-2-chloro-6-fluoro-phenyl)-6,6-dioxo-5-(2,2-difluoro-ethyl)-5,6-dihydro-6-thia-1,4-diaza-naphthalen-8-yl ester 1H-NMR (400 MHz, CDCl$_3$): 1.05 (6H, m), 2.65 (1H, m), 2.90 (2H, m), 4.80 (1H, t), 6.20 (1H, dt), 7.00 (1H, m), 7.70 (1H, m), 8.55 (1H, s), 8.60 (1H, s)

7-(3-Bromo-2-chloro-6-fluoro-phenyl)-6,6-dioxo-5-(2,2,2-trifluoro-ethyl)-5,6-dihydro-6-thia-1,4-diaza-naphthalen-8-ol 1H-NMR (400 MHz, CDCl$_3$): 4.60 (2H, m), 7.05 (1H, t), 7.70 (1H, m), 8.65 (1H, s), 8.75 (1H, s).

Example 4.5

Preparation of isobutyric acid 7-(3-bromo-2-chloro-6-fluoro-phenyl)-5-fluoro-6,6-dioxo-5,6-dihydro-6-thia-1,4-diaza-naphthalen-8-yl ester

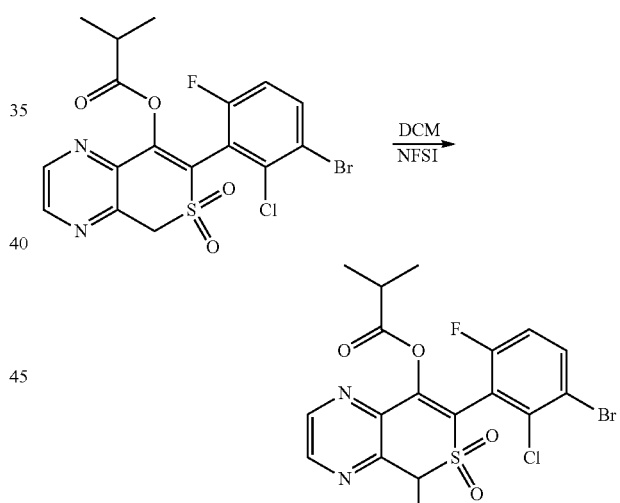

To a cooled (0 to 5° C.) solution of Compound No. X2 (Example 4.2) (0.13 g) in dichloromethane (1.5 ml) was added triethylamine (0.084 ml) followed by N-fluorobenzenesulfonimide ("NFSI") (0.172 g). The reaction mixture was allowed to warm to ambient temperature and stirred for 18 hours. Further triethylamine (0.042 ml) and N-fluorobenzenesulfonimide ("NFSI") (0.086 g) were added to the reaction mixture and stirred for 18 hours. The reaction mixture was concentrated and the residue purified by reverse phase chromatography (eluent: 0-100% v/v acetonitrile in water with 0.05% trifluoroacetic acid) to give isobutyric acid 7-(3-bromo-2-chloro-6-fluoro-phenyl)-5-fluoro-6,6-dioxo-5,6-dihydro-6-thia-1,4-diaza-naphthalen-8-yl ester (0.010 g)

1H-NMR (400 MHz, CDCl$_3$): 1.10 (6H, m), 2.70 (1H, m), 6.05 (1H, dd), 7.10 (1H, m), 7.80 (1H, m), 8.70 (1H, s), 8.80 (1H, s).

5. Reactions Which are Covered by Scheme 5

Example 5.1

Preparation of 3-[1-(2-chloro-6-trifluoromethyl-phenylmethanesulfonyl)-propyl]-pyrazine-2-carboxylic acid ethyl ester

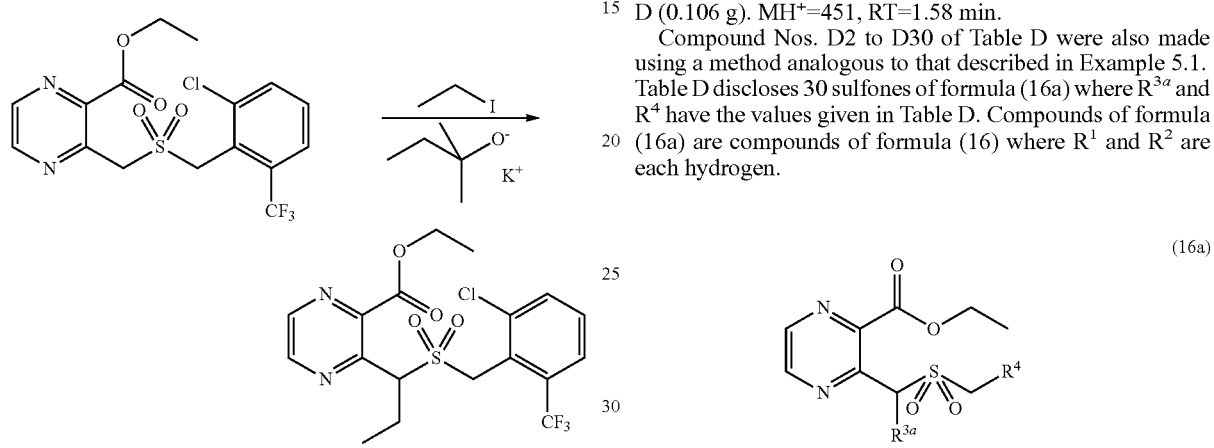

Potassium tert-pentoxide (0.155 ml, ~1.7M solution in toluene, Aldrich 60435) was added drop wise to a cooled (0 to 5° C.) solution of 3-(2-chloro-6-trifluoromethyl-phenylmethanesulfonylmethyl)-pyrazine-2-carboxylic acid ethyl ester (Compound B13 of Table B) (0.1 g) in N,N-dimethylformamide (1 ml) under nitrogen atmosphere and stirred cold for 20 minutes. Iodoethane (0.021 ml) was added to the cool dark red solution and stirred at this temperature for a further hour. The reaction mixture was partitioned between ether and 2M aqueous hydrochloric acid. The aqueous layer was extracted with further diethyl ether. The combined organic layers were washed further with water and brine, dried over magnesium sulfate and concentrated to give 3-[1-(2-chloro-6-trifluoromethyl-phenylmethanesulfonyl)-propyl]-pyrazine-2-carboxylic acid ethyl ester Compound No. D1 of Table D (0.106 g). MH$^+$=451, RT=1.58 min.

Compound Nos. D2 to D30 of Table D were also made using a method analogous to that described in Example 5.1. Table D discloses 30 sulfones of formula (16a) where R$^{3a}$ and R$^4$ have the values given in Table D. Compounds of formula (16a) are compounds of formula (16) where R$^1$ and R$^2$ are each hydrogen.

(16a)

TABLE D

| Comp. No. | R$^{3a}$ | R$^4$ | RT (min) | MH$^+$ | LC-MS Method |
|---|---|---|---|---|---|
| D1 | Et | 2-chloro-6-trifluoromethyl-phenyl- | 1.58 | 451 | A |
| D2 | HC≡C—H$_2$C— | 2-chloro-6-trifluoromethyl-phenyl- | 1.47 | 461 | A |
| D3 | Me | 2-chloro-6-trifluoromethyl-phenyl- | 1.49 | 437 | A |
| D4 | F$_2$HC—H$_2$C— | 2-chloro-6-trifluoromethyl-phenyl- | 1.58 | 486 | A |
| D5 | HC≡C—H$_2$C— | 5-chloro-2-trifluoromethyl-phenyl- | 1.70 | 461 | A |
| D6 | Et | 5-chloro-2-trifluoromethyl-phenyl- | 1.66 | 451 | A |
| D7 | F$_2$HC—H$_2$C— | 5-chloro-2-trifluoromethyl-phenyl- | 1.59 | 487 | A |
| D8 | HC≡C—H$_2$C— | 3-bromo-2-chloro-6-fluoro-phenyl- | 1.61 | 490 | A |
| D9 | F$_2$HC—H$_2$C— | 3-bromo-2-chloro-6-fluoro-phenyl- | 1.63 | 516 | A |
| D10 | Et | 3-bromo-2-chloro-6-fluoro-phenyl- | 1.61 | 480 | A |
| D11 | Me | 3-bromo-2-chloro-6-fluoro-phenyl- | 1.53 | 466 | A |
| D12 | HC≡C—H$_2$C— | 4-bromo-2-trifluoromethyl-phenyl- | 1.76 | 506 | A |
| D13 | F$_2$HC—H$_2$C— | 4-bromo-2-trifluoromethyl-phenyl- | 1.53 | 532 | A |
| D14 | Et | 4-bromo-2-trifluoromethyl-phenyl- | 1.69 | 496 | A |
| D15 | Me | 4-bromo-2-trifluoromethyl-phenyl- | — | — | A |
| D16 | HC≡C—H$_2$C— | 2,4,6-trimethyl-phenyl- | 1.59 | 401 | A |
| D17 | F$_2$HC—H$_2$C— | 2,4,6-trimethyl-phenyl- | 1.63 | 427 | A |
| D18 | Et | 2,4,6-trimethyl-phenyl- | 1.45 | — | A |
| D19 | Me | 2,4,6-trimethyl-phenyl- | 1.52 | 376 | A |
| D20 | Allyl | 3-bromo-2-chloro-6-fluoro-phenyl- | 1.60 | 491 | A |
| D21 | H$_3$C—C≡C—H$_2$C— | 3-bromo-2-chloro-6-fluoro-phenyl- | 1.59 | 503 | A |
| D22 | n-Pr | 3-bromo-2-chloro-6-fluoro-phenyl- | 1.63 | 493 | A |
| D23 | MeO—CH$_2$— | 3-bromo-2-chloro-6-fluoro-phenyl- | 1.52 | 495 | A |
| D24 | Ph—CH$_2$—O—CH$_2$— | 3-bromo-2-chloro-6-fluoro-phenyl- | 1.78 | 571 | A |
| D25 | ClCH$_2$—CH$_2$—CH$_2$— | 3-bromo-2-chloro-6-fluoro-phenyl- | 1.63 | 527 | A |
| D26 | ClCH$_2$—CH$_2$—CH$_2$—CH$_2$— | 3-bromo-2-chloro-6-fluoro-phenyl- | 1.70 | 541 | A |
| D27 | Ph—CH$_2$— | 3-bromo-2-chloro-6-fluoro-phenyl- | 1.72 | 541 | A |
| D28 | (2-chloro-thiophene)-5-CH$_2$— | 3-bromo-2-chloro-6-fluoro-phenyl- | 1.80 | 581 | A |
| D29 | F$_3$C—H$_2$C— | 2,4,6-trimethyl-phenyl- | 1.77 | 445 | A |
| D30 | F$_2$HC—H$_2$C— | 2,6-dichloro-3-trifluoromethyl-phenyl- | 1.70 | 521 | A |

Example 5.2

Preparation of 7-(2-chloro-6-trifluoromethyl-phenyl)-5-ethyl-6,6-dioxo-5,6-dihydro-6-thia-1,4-diaza-naphthalen-8-ol (Compound No. E1 of Table E)

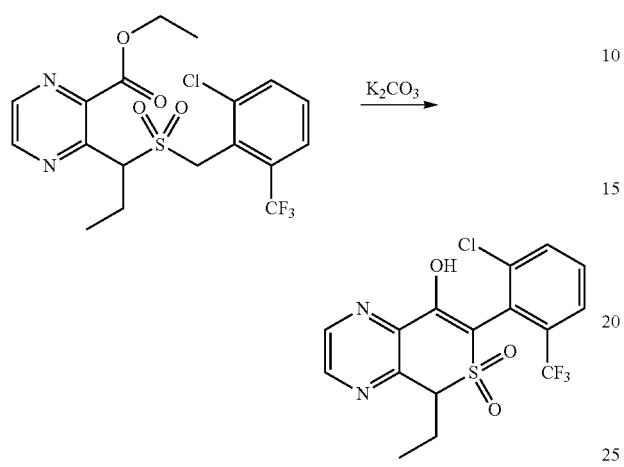

A mixture of 3-[1-(2-chloro-6-trifluoromethyl-phenyl-methanesulfonyl)-propyl]-pyrazine-2-carboxylic acid ethyl ester (0.106 g) and potassium carbonate (0.081 g) in N,N-dimethylformamide (2 ml) was heated to 120° C. for 1 hour. The reaction mixture was cooled to ambient temperature, diluted with water and washed with diethyl ether. The aqueous layer was acidified with aqueous hydrochloric acid (2M) and extracted with ethyl acetate (2×20 ml). The organic layer was concentrated and the residue purified by reverse phase chromatography (eluent: 0-100% v/v acetonitrile in water with 0.05% trifluoroacetic acid) to give 7-(2-chloro-6-trifluoromethyl-phenyl)-5-ethyl-6,6-dioxo-5,6-dihydro-6-thia-1,4-diaza-naphthalen-8-ol Compound No. E1 of Table E (0.042 g). $MH^+$=405, RT=1.38 min.

Compound Nos. E1 to E24 of Table E were made using a method analogous to that described in Example 5.2.

Table E discloses 24 6,6-dioxo-6-thia-1,4-diaza-naphthalenes of formula (14a) where $R^{3a}$ and $R^4$ have the values given in Table E. Compounds of formula (14a) are compounds of formula (14) where $R^1$ and $R^2$ are each hydrogen.

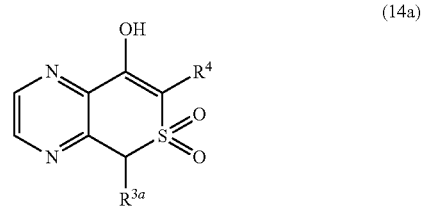

(14a)

TABLE E

| Comp. No. | $R^{3a}$ | $R^4$ | RT (min) | $MH^+$ | LC-MS Method |
|---|---|---|---|---|---|
| E1 | Et | 2-chloro-6-trifluoromethyl-phenyl- | 1.38 | 405 | A |
| E2 | HC≡C—H₂C— | 2-chloro-6-trifluoromethyl-phenyl- | 1.44 | 415 | A |
| E3 | Me | 2-chloro-6-trifluoromethyl-phenyl- | 1.29 | 391 | A |
| E4 | F₂HC—H₂C— | 2-chloro-6-trifluoromethyl-phenyl- | 1.44 | 441 | A |
| E5 | HC≡C—H₂C— | 5-chloro-2-trifluoromethyl-phenyl- | 1.37 | 415 | A |
| E6 | Et | 5-chloro-2-trifluoromethyl-phenyl- | 1.41 | 405 | A |
| E7 | F₂HC—H₂C— | 5-chloro-2-trifluoromethyl-phenyl- | 1.47 | 441 | A |
| E8 | HC≡C—H₂C— | 3-bromo-2-chloro-6-fluoro-phenyl- | 1.48 | 444 | A |
| E9 | F₂HC—H₂C— | 3-bromo-2-chloro-6-fluoro-phenyl- | 1.50 | 470 | A |
| E10 | Et | 3-bromo-2-chloro-6-fluoro-phenyl- | 1.43 | 434 | A |
| E11 | Me | 3-bromo-2-chloro-6-fluoro-phenyl- | 1.35 | 420 | A |
| E12 | HC≡C—H₂C— | 4-bromo-2-trifluoromethyl-phenyl- | 1.47 | 459 | A |
| E13 | F₂HC—H₂C— | 4-bromo-2-trifluoromethyl-phenyl- | 1.51 | 485 | A |
| E14 | Et | 4-bromo-2-trifluoromethyl-phenyl- | 1.45 | 449 | A |
| E15 | Me | 4-bromo-2-trifluoromethyl-phenyl- | 1.37 | 435 | A |
| E16 | HC≡C—H₂C— | 2,4,6-trimethyl-phenyl- | 1.48 | 355 | A |
| E17 | F₂HC—H₂C— | 2,4,6-trimethyl-phenyl- | 1.55 | 381 | A |
| E18 | Et | 2,4,6-trimethyl-phenyl- | 1.44 | 345 | A |
| E19 | Me | 2,4,6-trimethyl-phenyl- | 1.38 | 331 | A |
| E20 | Allyl | 3-bromo-2-chloro-6-fluoro-phenyl- | 1.41 | 447 | A |
| E21 | H₃C—C≡C—H₂C— | 3-bromo-2-chloro-6-fluoro-phenyl- | 1.41 | 459 | A |
| E22 | n-Pr | 3-bromo-2-chloro-6-fluoro-phenyl- | 1.47 | 449 | A |
| E23 | Ph—CH₂— | 3-bromo-2-chloro-6-fluoro-phenyl- | 1.54 | 497 | A |
| E24 | (2-chloro-thiophene)-5-CH₂— | 3-bromo-2-chloro-6-fluoro-phenyl- | 1.63 | 536 | A |

Example 5.3

Preparation of 5,5-dimethyl-6,6-dioxo-7-(2,4,6-trimethyl-phenyl)-5,6-dihydro-6-thia-1,4-diaza-naphthalen-8-ol

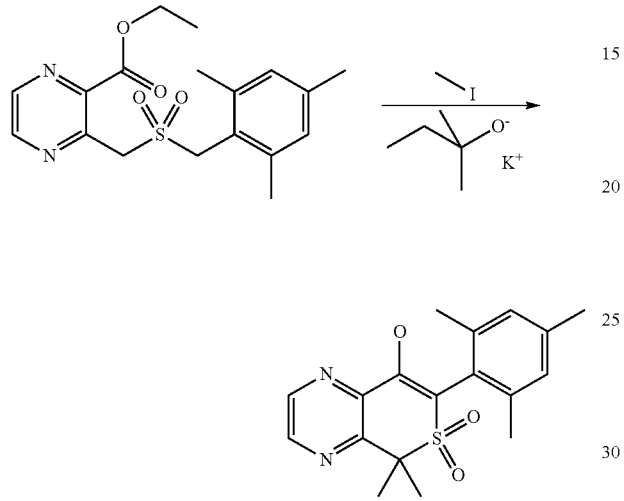

Potassium tent-pentoxide (0.18 ml, ~1.7M solution in toluene, Aldrich 60435) was added drop wise to a cooled (0 to 5° C.) solution of 3-(2,4,6-trimethyl-phenylmethanesulfonylmethyl)-pyrazine-2-carboxylic acid ethyl ester (Compound B20 of Table B) (0.1 g) in N,N-dimethylformamide (1 ml) under nitrogen atmosphere and stirred cold for 20 minutes. Iodomethane (0.016 ml) was added to the cool dark red solution and stirred at this temperature for a further hour. Further potassium tert-pentoxide (0.18 ml, ~1.7M solution in toluene) was added drop wise to the cooled (0 to 5° C.) solution and stirred cold for 20 minutes. Further iodomethane (0.016 ml) was added and the reaction stirred at this temperature for another hour. The reaction mixture was warmed to ambient temperature and further potassium tert-pentoxide (0.18 ml, ~1.7M solution in toluene) was added drop wise and stirred for 4 hours. The reaction mixture was partitioned between ethyl acetate and 2M aqueous hydrochloric acid. The organic layer was concentrated and the residue purified by reverse phase chromatography (eluent: 0-100% v/v acetonitrile in water with 0.05% trifluoroacetic acid) to give 5,5-dimethyl-6,6-dioxo-7-(2,4,6-trimethyl-phenyl)-5,6-dihydro-6-thia-1,4-diaza-naphthalen-8-ol Compound No. F1 of Table F (0.037 g). $MH^+=345$, RT=1.42 min.

Compound Nos. F1 to F9 of Table F were made using the method described in Example 5.3.

Example 5.4

Preparation of 7-(2-chloro-6-trifluoromethyl-phenyl)-5-methyl-6,6-dioxo-5-prop-2-ynyl-5,6-dihydro-6-thia-1,4-diaza-naphthalen-8-ol

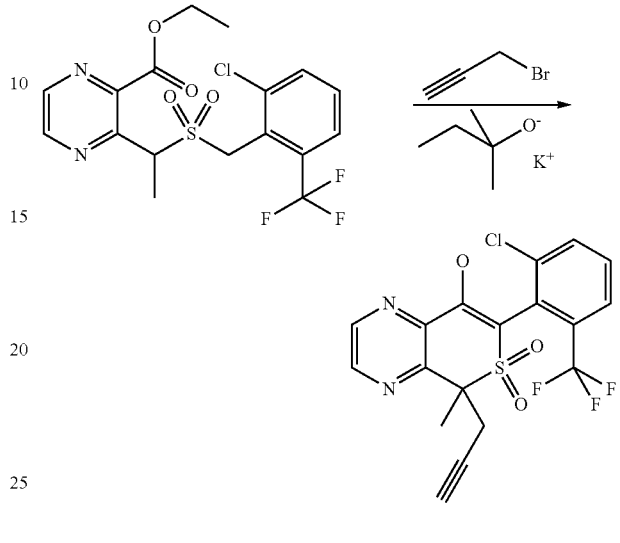

Potassium tent-pentoxide (0.216 ml, ~1.7M solution in toluene, Aldrich 60435) was added drop wise to a cooled (0 to 5° C.) solution of Compound No. D3 of Table D (0.146 g) in N,N-dimethylformamide (2 ml) under nitrogen atmosphere and stirred cold for 20 minutes. Propargyl bromide (0.04 ml, of an 80% solution in toluene) was added to the cool dark red solution and stirred at this temperature for a further hour. The reaction mixture was warmed to ambient temperature and further potassium tert-pentoxide (0.216 ml, ~1.7M solution in toluene) was added drop wise and stirred for 4 hours. The reaction mixture was partitioned between ethyl acetate and 2M aqueous hydrochloric acid. The organic layer was concentrated and the residue purified by reverse phase chromatography (eluent: 0-100% v/v acetonitrile in water with 0.05% trifluoroacetic acid) to give 7-(2-chloro-6-trifluoromethyl-phenyl)-5-methyl-6,6-dioxo-5-prop-2-ynyl-5,6-dihydro-6-thia-1,4-diaza-naphthalen-8-ol Compound No. F10 of Table F (0.061 g). $MH^+=429$, RT=1.39 min.

Compound No. F9 of Table F can also be made using a method analogous to that described in Example 5.4.

Table F discloses 11 6,6-dioxo-6-thia-1,4-diaza-naphthalenes of formula (15a) where $R^{3a}$, $R^{3b}$ and $R^4$ have the values given in Table F. Compounds of formula (15a) are compounds of formula (15) where $R^1$ and $R^2$ are each hydrogen.

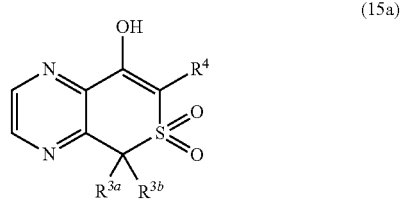

(15a)

TABLE F

| Comp. No. | R$^{3a}$ | R$^{3b}$ | R$^4$ | RT (min) | MH$^+$ | LC-MS Method | 1H-NMR (400 MHz, chemical shifts in ppm) |
|---|---|---|---|---|---|---|---|
| F1 | Me | Me | 2,4,6-trimethyl-phenyl- | 1.42 | 345 | A | |
| F2 | Me | Me | 3-bromo-2-chloro-6-fluoro-phenyl- | 1.43 | 434 | A | |
| F3 | Me | Me | 2-chloro-5-fluoro-phenyl- | 1.35 | 355 | A | |
| F4 | —CH$_2$—CH$_2$— | | 2-chloro-6-trifluoromethyl-phenyl- | 1.48 | 403 | A | |
| F5 | Me | Me | 5-chloro-2-trifluoromethyl-phenyl- | 1.41 | 405 | A | |
| F6 | Me | Me | 4-bromo-2-trifluoromethyl-phenyl- | — | — | — | 8.80-8.82 (m, 2H), 8.03 (d, 1H), 7.96-7.99 (dd, 1H), 7.39 (d, 1H), 1.73 (s, 3H), 1.64 (s, 3H). d$_6$-DMSO |
| F7 | —CH$_2$—CH$_2$—CH$_2$— | | 3-bromo-2-chloro-6-fluoro-phenyl- | 1.25 | 445 | A | |
| F8 | —CH$_2$—CH$_2$—CH$_2$—CH$_2$— | | 3-bromo-2-chloro-6-fluoro-phenyl- | 1.48 | 461 | A | |
| F9 | Me | Me | 2-chloro-6-trifluoromethyl-phenyl- | 1.33 | 405 | A | |
| F10 | Me | HC≡C—H$_2$C— | 2-chloro-6-trifluoromethyl-phenyl- | 1.39 | 429 | A | |
| F11 | —CH$_2$—CH$_2$— | | 5-chloro-2-trifluoromethyl-phenyl- | 1.44 | 403 | A | |

6. Reactions Which are Covered by Scheme 6

Example 6.1

Preparation of thioacetic acid S-(2-bromo-benzyl) ester

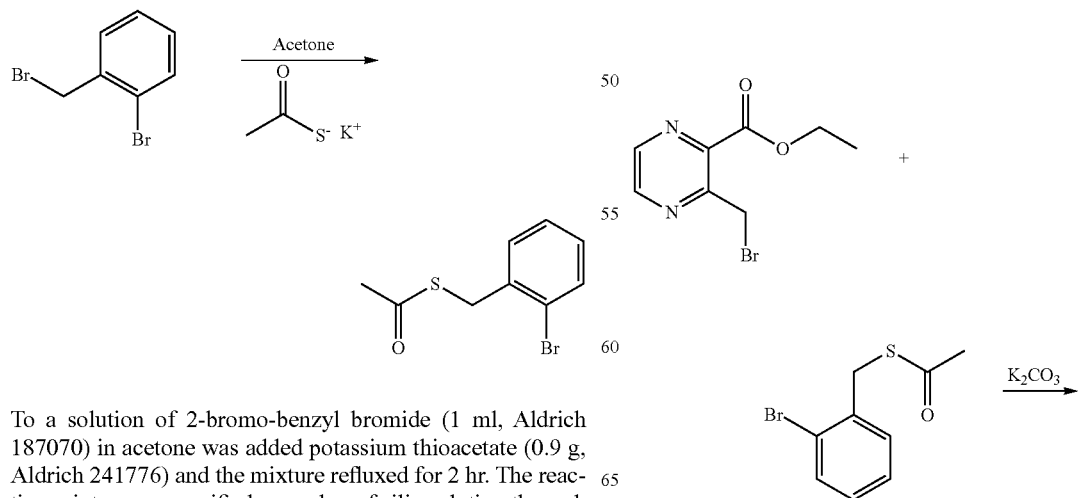

To a solution of 2-bromo-benzyl bromide (1 ml, Aldrich 187070) in acetone was added potassium thioacetate (0.9 g, Aldrich 241776) and the mixture refluxed for 2 hr. The reaction mixture was purified on a plug of silica eluting through with further acetone to give thioacetic acid S-(2-bromo-benzyl) ester (1.57 g) 1H-NMR (400 MHz, CDCl$_3$): 2.34 (3H, s), 4.24 (2H, s), 7.09-7.14 (1H, dt), 7.23-7.27 (1H, dt), 7.44-7.46 (1H, dd), 7.54-7.56 (1H, dd).

Example 6.2

Preparation of 3-(2-bromo-benzylsulfanylmethyl)-pyrazine-2-carboxylic acid methyl ester

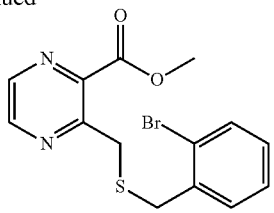

To a solution of thioacetic acid S-(2-bromo-benzyl) ester (1.57 g) in methanol (20 ml) was added potassium carbonate (1.1 g) and the mixture stirred for 30 min. 3-bromomethyl-pyrazine-2-carboxylic acid ethyl ester (0.75 g) was added to the reaction mixture and the whole heated to reflux. After 2 hr the reaction mixture was concentrated, partitioned between ethyl acetate and 2M aqueous hydrochloric acid. The organic layer was purified on a plug of silica eluting through with acetone to give on evaporation a sticky solid. The solid was triturated with dichloromethane to give a solid (0.758 g) which was 3-(2-bromo-benzylsulfanylmethyl)-pyrazine-2-carboxylic acid, MH$^+$=339, RT=1.30 min (Method A). This compound can be esterified to the desired compound by methods known to persons skilled in the art. The dichloromethane filtrate was concentrated and the residue purified by chromatography on silica gel (eluent: 0-20% v/v ethyl acetate in dichloromethane) to give 3-(2-bromo-benzylsulfanylmethyl)-pyrazine-2-carboxylic acid methyl ester (0.206 g) a transesterification having taken place in the process. MH$^+$=354, RT=1.52 min (Method A).

Example 6.3

Preparation of 3-(2',4'-dichloro-3-ethyl-biphenyl-4-ylmethylsulfanylmethyl)-pyrazine-2-carboxylic acid ethyl ester

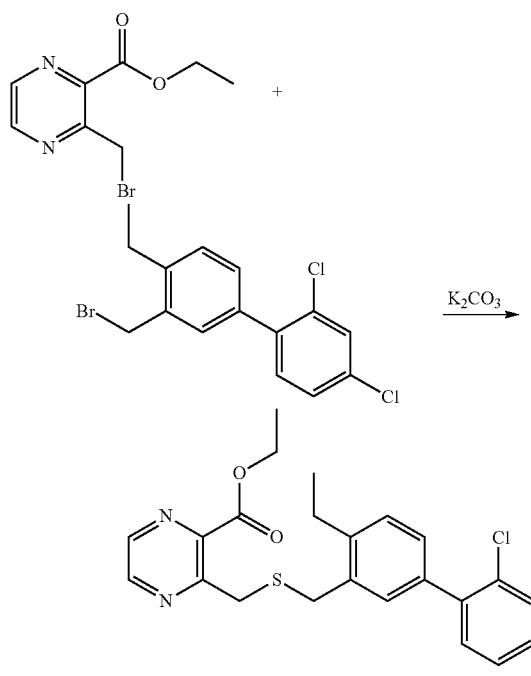

To a solution of 3'-bromomethyl-2,4-dichloro-4'-ethyl-biphenyl (1 g) in ethanol (10 ml) was added potassium thioacetate (1.1 g, Aldrich 241776) and the mixture stirred for 1 hr. To this mixture was added potassium carbonate (0.442 g) and stirring was continued for a further hour. A solution of 3-bromomethyl-pyrazine-2-carboxylic acid ethyl ester (0.712 g) in ethanol (3 ml) was added to the reaction mixture and the reaction was stirred for a further 18 hr. The reaction was partitioned between chloroform and water. The organic layer was concentrated and the residue purified by chromatography on silica gel (eluent: 0-20% v/v ethyl acetate in dichloromethane) to give a 30% pure sample of 3-(2',4'-dichloro-3-ethyl-biphenyl-4-ylmethylsulfanylmethyl)-pyrazine-2-carboxylic acid ethyl ester contaminated with 3-bromomethyl-pyrazine-2-carboxylic acid ethyl ester (0.300 g). MH$^+$=461, RT=2.25 min (Method A).

Compound Nos. A30 and A31 of Table A were also made using methods analogous to that described in Example 6.3.

BIOLOGICAL EXAMPLES

Example B1

Herbicidal Action Post-Emergence

Seeds of a variety of test species were sown in standard soil in pots. After 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown under controlled conditions in a glasshouse (at 24/16° C., day/night; 14 hours light; 65% humidity) and watered twice daily. After 13 days, the test was evaluated and the assessed scores, from 10 to 0, are tabulated in Table B1 (10=total damage to plant; 0=no damage to plant).

TABLE B1

| | Application post-emergence | | | | |
| --- | --- | --- | --- | --- | --- |
| Comp No. | Rate(g/ha) | SOLNI | AMARE | SETFA | ECHCG | IPOHE |
| C1 | 1000 | 8 | 10 | 8 | 7 | 8 |
| C2 | 1000 | 0 | 0 | 0 | 0 | 0 |
| C3 | 1000 | 0 | 0 | 0 | 0 | 0 |
| C4 | 1000 | 4 | 7 | 5 | 3 | 2 |
| C5 | 1000 | 4 | 3 | 4 | 1 | 3 |
| C6 | 1000 | 3 | 4 | 2 | 1 | 0 |
| C7 | 1000 | 8 | 8 | 8 | 6 | 7 |
| C8 | 1000 | 7 | 5 | 5 | 3 | 1 |
| C9 | 1000 | 4 | 6 | 7 | 3 | 1 |
| C10 | 1000 | 8 | 6 | 6 | 5 | 6 |
| C11 | 1000 | 7 | 7 | 7 | 5 | 5 |
| C12 | 1000 | 8 | 8 | 6 | 3 | 6 |
| C13 | 1000 | 2 | 8 | 8 | 8 | 8 |
| C14 | 1000 | 7 | 8 | 7 | 7 | 8 |
| C15 | 1000 | 8 | 7 | 6 | 5 | 3 |
| C16 | 1000 | 10 | 9 | 3 | 5 | 7 |
| C17 | 1000 | 10 | 10 | 8 | 8 | 7 |
| C18 | 1000 | 8 | 7 | 8 | 8 | 8 |
| C19 | 1000 | 9 | 7 | 8 | 7 | 8 |
| C20 | 1000 | 7 | 1 | 4 | 4 | 7 |
| C21 | 1000 | 10 | 9 | 7 | 7 | 8 |
| C22 | 1000 | 9 | 10 | 5 | 5 | 7 |
| C23 | 1000 | 9 | 8 | 7 | 8 | 8 |
| C24 | 1000 | 6 | 10 | 10 | 7 | 3 |
| E1 | 1000 | 9 | 9 | 8 | 7 | 7 |
| E2 | 1000 | 8 | 10 | 8 | 8 | 8 |
| E3 | 1000 | 8 | 9 | 8 | 8 | 8 |

TABLE B1-continued

Application post-emergence

| Comp No. | Rate(g/ha) | SOLNI | AMARE | SETFA | ECHCG | IPOHE |
|---|---|---|---|---|---|---|
| E4 | 1000 | 8 | 9 | 6 | 6 | 7 |
| E6 | 1000 | 8 | 8 | 3 | 5 | 7 |
| E7 | 250 | 7 | 6 | 2 | 2 | 7 |
| E9 | 1000 | 9 | 10 | 5 | 3 | 8 |
| E10 | 250 | 7 | 7 | 7 | 4 | 8 |
| E11 | 1000 | 10 | 8 | 8 | 8 | 9 |
| E14 | 1000 | 10 | 9 | 6 | 7 | 7 |
| E16 | 1000 | 8 | 5 | 2 | 2 | 5 |
| E17 | 1000 | 7 | 10 | 10 | 10 | 7 |
| E19 | 1000 | 8 | 3 | 5 | 5 | 7 |
| E21 | 1000 | 9 | 6 | 4 | 7 | 8 |
| E23 | 1000 | 8 | 6 | 4 | 8 | 6 |
| E24 | 1000 | 7 | 6 | 0 | 0 | 5 |
| F1 | 1000 | 10 | 10 | 8 | 8 | 8 |
| F2 | 1000 | 10 | 10 | 9 | 8 | 9 |
| F4 | 1000 | 9 | 9 | 8 | 6 | 7 |
| F5 | 1000 | 10 | 10 | 6 | 8 | 9 |
| F6 | 250 | 9 | 9 | 8 | 9 | 8 |
| F7 | 1000 | 5 | 4 | 1 | 1 | 6 |
| F9 | 1000 | 8 | 9 | 8 | 8 | 9 |
| F11 | 1000 | 7 | 6 | 2 | 3 | 7 |
| X1 | 1000 | 8 | 6 | 6 | 2 | 7 |
| X2 | 1000 | 10 | 10 | 8 | 8 | 8 |

Example B2

Herbicidal Action Post-Emergence

Seeds of crop and representative weed species were sown in standard soil in pots. After cultivation for 14 days under controlled conditions in a glasshouse (at 22/16° C., day/night; 16 hours light; 65% humidity), the plants were sprayed. The spray solution was prepared by dissolving the technical active ingredient in acetone containing 10.56 wt % Emulsogen EL, 42.22 wt % N-methylpyrrolidone and 2.22 wt % DPG-monoethyl ether to give a 5% stock solution. This was then diluted with water containing 0.2% (v/v) of the adjuvant X-77 to give the desired treatment concentration.

The test plants were then grown on under controlled conditions in a glasshouse (at 22/16° C., day/night; 16 hours light; 65% humidity) and watered twice daily. After 15 days the test was evaluated and the assessed scores, from 10 to 0, are tabulated in Table B2 (10=total damage to plant; 0=no damage to plant).

TABLE B2

Application post-emergence

| Comp No. | Rate(g/ha) | AMARE | SETFA | ECHCG | IPOHE |
|---|---|---|---|---|---|
| E8 | 500 | 8 | 6 | 6 | 9 |
| E20 | 500 | 7 | 4 | 2 | 7 |
| E22 | 500 | 7 | 2 | 0 | 7 |
| F3 | 500 | 7 | 4 | 4 | 8 |
| F8 | 500 | 5 | 5 | 6 | 8 |
| F10 | 500 | 8 | 8 | 7 | 9 |

Key: SOLNI = *Solanum nigrum*; AMARE = *Amaranthus retroflexus*; SETFA = *Setaria faberi*; ECHCG = *Echinochloa crus-galli*; EPOHE = *Ipomea hederaceae*.

The invention claimed is:

1. A compound of formula (I)

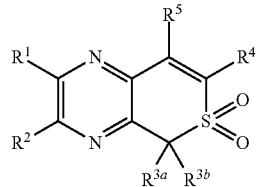

wherein
$R^1$ and $R^2$ are independently hydrogen, halogen, cyano, $C_1$-$C_8$alkyl, $C_1$-$C_8$haloalkyl, hydroxy, $C_1$-$C_8$alkoxy-, thiol, or $C_1$-$C_8$alkylthio-;
$R^{3a}$ and $R^{3b}$ are independently hydrogen, halogen, cyano, $C_1$-$C_8$alkyl, $C_1$-$C_8$alkoxy-$C_1$-$C_4$alkyl-, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_3$-$C_{10}$cycloalkyl, $C_3$-$C_{10}$cycloalkyl-$C_1$-$C_4$alkyl-, heterocyclyl, heterocyclyl-$C_1$-$C_4$alkyl-, or $C_1$-$C_8$alkoxycarbonyl-, or
$R^{3a}$ and $R^{3b}$ together with the carbon atom they are attached to join to form a 3- to 10-membered carbocyclic ring or a 3- to 10-membered heterocyclic ring;
$R^4$ is aryl or aryl substituted by one to five $R^6$, or heteroaryl or heteroaryl substituted by one to five $R^6$;
$R^5$ is hydroxy or $R^8$-oxy-, and where $R^8$ is $C_1$-$C_8$alkyl-, $C_2$-$C_8$alkenyl-, $C_2$-$C_8$alkynyl-, aryl-$C_1$-$C_4$alkyl- or aryl-$C_1$-$C_4$alkyl- where the aryl moiety is substituted by one to five $R^9$, $C_1$-$C_8$alkylcarbonyl-, $C_1$-$C_8$alkoxycarbonyl-, $C_1$-$C_8$alkylthiocarbonyl-, or $C_1$-$C_8$alkylsulfonyl-; and where each $R^9$ is independently halogen, cyano, nitro, $C_1$-$C_8$alkyl, $C_1$-$C_8$haloalkyl, $C_1$-$C_8$alkoxy- or $C_1$-$C_8$haloalkoxy-;
each $R^6$ is independently halogen, cyano, nitro, $C_1$-$C_8$alkyl, $C_1$-$C_8$alkoxy-$C_1$-$C_4$alkyl-, $C_1$-$C_8$haloalkyl, $C_1$-$C_8$haloalkoxy-$C_1$-$C_4$alkyl-, hydroxy, $C_1$-$C_8$alkoxy-, $C_1$-$C_8$haloalkoxy-, thiol, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, amino, N—$C_1$-$C_8$alkylcarbonylamino-, N—$C_1$-$C_8$alkyl-N—$C_1$-$C_8$alkylcarbonylamino-, N—$C_1$-$C_8$alkylsulfonylamino-, N—$C_1$-$C_8$alkyl-N—$C_1$-$C_8$alkylsulfonylamino-, aryl or aryl substituted by one to five $R^7$, heteroaryl or heteroaryl substituted by one to five $R^7$, aryloxy- or aryloxy- substituted by one to five $R^7$, heteroaryloxy- or heteroaryloxy- substituted by one to five $R^7$, arylthio- or arylthio-substituted by one to five $R^7$, or heteroarylthio- or heteroarylthio- substituted by one to five $R^7$; and
each $R^7$ is independently halogen, cyano, nitro, $C_1$-$C_8$alkyl, $C_1$-$C_8$haloalkyl, $C_1$-$C_8$alkoxy- or $C_1$-$C_8$haloalkoxy-;
or a salt or N-oxide thereof.

2. A compound according to claim 1 where $R^1$ is hydrogen, halogen or $C_1$-$C_8$alkyl.

3. A compound according to claim 1 where $R^2$ is hydrogen, halogen or $C_1$-$C_8$alkyl.

4. A compound according to claim 1 where $R^{3a}$ is hydrogen, halogen, $C_1$-$C_8$alkyl, $C_1$-$C_8$haloalkyl or $C_2$-$C_8$alkynyl.

5. A compound according to claim 1 where $R^{3b}$ is hydrogen, halogen, $C_1$-$C_8$alkyl, $C_1$-$C_8$haloalkyl or $C_2$-$C_8$alkynyl.

6. A compound according to claim 1 where $R^4$ is phenyl or phenyl substituted by one to five $R^6$, or heteroaryl or heteroaryl substituted by one to five $R^6$ (where heteroaryl is pyridyl, pyrimidinyl, pyrazolyl, triazolyl, thiophenyl, isoxazolyl, oxadiazolyl, or thiazolyl).

7. A herbicidal composition which comprises a herbicidally effective amount of a compound according to claim 1 in addition to formulation adjuvants.

8. A method of controlling plants which comprises applying to the plants or to the locus thereof a herbicidally effective amount of a compound according to claim 1.

9. A compound of formula (10):

(10)

where $R^1$ and $R^2$ are independently hydrogen, halogen, cyano, $C_1$-$C_8$alkyl, $C_1$-$C_8$haloalkyl, hydroxy, $C_1$-$C_8$alkoxy-, thiol, or $C_1$-$C_8$alkylthio-;
$R^4$ is aryl or aryl substituted by one to five $R^6$, or heteroaryl or heteroaryl substituted by one to five $R^6$;
each $R^6$ is independently halogen, cyano, nitro, $C_1$-$C_8$alkyl, $C_1$-$C_8$alkoxy-$C_1$-$C_4$alkyl-, $C_1$-$C_8$haloalkyl, $C_1$-$C_8$haloalkoxy-$C_1$-$C_4$alkyl-, hydroxy, $C_1$-$C_8$alkoxy-, $C_1$-$C_8$haloalkoxy-, thiol, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, amino, N—$C_1$-$C_8$alkylcarbonylamino-, N—$C_1$-$C_8$alkyl-N—$C_1$-$C_8$alkylcarbonylamino-, N—$C_1$-$C_8$alkylsulfonylamino-, N—$C_1$-$C_8$alkyl-N—$C_1$-$C_8$alkylsulfonylamino-, aryl or aryl substituted by one to five $R^7$, heteroaryl or heteroaryl substituted by one to five $R^7$, aryloxy- or aryloxy- substituted by one to five $R^7$, heteroaryloxy- or heteroaryloxy- substituted by one to five $R^7$, arylthio- or arylthio- substituted by one to five $R^7$, or heteroarylthio- or heteroarylthio- substituted by one to five $R^7$; and
each $R^7$ is independently halogen, cyano, nitro, $C_1$-$C_8$alkyl, $C_1$-$C_8$haloalkyl, $C_1$-$C_8$alkoxy- or $C_1$-$C_8$haloalkoxy-;
or a salt or N-oxide thereof.

10. A compound of formula (6):

(6)

where $R^1$ and $R^2$ are independently hydrogen, halogen, cyano, $C_1$-$C_8$alkyl, $C_1$-$C_8$haloalkyl, hydroxy, $C_1$-$C_8$alkoxy-, thiol, or $C_1$-$C_8$alkylthio-;
$R^4$ is aryl or aryl substituted by one to five $R^6$, or heteroaryl or heteroaryl substituted by one to five $R^6$;
each $R^6$ is independently halogen, cyano, nitro, $C_1$-$C_8$alkyl, $C_1$-$C_8$alkoxy-$C_1$-$C_4$alkyl-, $C_1$-$C_8$haloalkyl, $C_1$-$C_8$haloalkoxy-$C_1$-$C_4$alkyl-, hydroxy, $C_1$-$C_8$alkoxy-, $C_1$-$C_8$haloalkoxy-, thiol, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, amino, N—$C_1$-$C_8$alkylcarbonylamino-, N—$C_1$-$C_8$alkyl-N—$C_1$-$C_8$alkylcarbonylamino-, N—$C_1$-$C_8$alkylsulfonylamino-, N—$C_1$-$C_8$alkyl-N—$C_1$-$C_8$alkylsulfonylamino-, aryl or aryl substituted by one to five $R^7$, heteroaryl or heteroaryl substituted by one to five $R^7$, aryloxy- or aryloxy- substituted by one to five $R^7$, heteroaryloxy- or heteroaryloxy- substituted by one to five $R^7$, arylthio- or arylthio- substituted by one to five $R^7$, or heteroarylthio- or heteroarylthio- substituted by one to five $R^7$;
each $R^7$ is independently halogen, cyano, nitro, $C_1$-$C_8$alkyl, $C_1$-$C_8$haloalkyl, $C_1$-$C_8$alkoxy- or $C_1$-$C_8$haloalkoxy-; and
$R^{10}$ is $C_1$-$C_8$alkyl;
or a salt or N-oxide thereof.

11. A compound of formula (9):

(9)

where $R^1$ and $R^2$ are independently hydrogen, halogen, cyano, $C_1$-$C_8$alkyl, $C_1$-$C_8$haloalkyl, hydroxy, $C_1$-$C_8$alkoxy-, thiol, or $C_1$-$C_8$alkylthio-;
$R^4$ is aryl or aryl substituted by one to five $R^6$, or heteroaryl or heteroaryl substituted by one to five $R^6$;
each $R^6$ is independently halogen, cyano, nitro, $C_1$-$C_8$alkyl, $C_1$-$C_8$alkoxy-$C_1$-$C_4$alkyl-, $C_1$-$C_8$haloalkyl, $C_1$-$C_8$haloalkoxy-$C_1$-$C_4$alkyl-, hydroxy, $C_1$-$C_8$alkoxy-, $C_1$-$C_8$haloalkoxy-, thiol, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, amino, N—$C_1$-$C_8$alkylcarbonylamino-, N—$C_1$-$C_8$alkyl-N—$C_1$-$C_8$alkylcarbonylamino-, N—$C_1$-$C_8$alkylsulfonylamino-, N—$C_1$-$C_8$alkyl-N—$C_1$-$C_8$alkylsulfonylamino-, aryl or aryl substituted by one to five $R^7$, heteroaryl or heteroaryl substituted by one to five $R^7$, aryloxy- or aryloxy- substituted by one to five $R^7$, heteroaryloxy- or heteroaryloxy- substituted by one to five $R^7$, arylthio- or arylthio- substituted by one to five $R^7$, or heteroarylthio- or heteroarylthio- substituted by one to five $R^7$;
each $R^7$ is independently halogen, cyano, nitro, $C_1$-$C_8$alkyl, $C_1$-$C_8$haloalkyl, $C_1$-$C_8$alkoxy- or $C_1$-$C_8$haloalkoxy-; and
$R^{10}$ is $C_1$-$C_8$alkyl;
or a salt or N-oxide thereof.

* * * * *